United States Patent
Alexandrov et al.

(10) Patent No.: US 9,920,328 B2
(45) Date of Patent: Mar. 20, 2018

(54) SEQUENCE DETERMINED DNA FRAGMENTS AND CORRESPONDING POLYPEPTIDES ENCODED THEREBY

(71) Applicant: CERES, INC., Thousand Oaks, CA (US)

(72) Inventors: Nickolai Alexandrov, Thousand Oaks, CA (US); Vyacheslav Brover, Simi Valley, CA (US); Kenneth A. Feldmann, Tucson, AZ (US); Vladimir Makarov, Thousand Oaks, CA (US); Timothy J. Swaller, Thousand Oaks, CA (US); Gregory Nadzan, Woodland Hills, CA (US); Peter Mascia, Thousand Oaks, CA (US); Maxim Troukhan, Agoura Hills, CA (US); Joel Rarang, Granada Hills, CA (US); James Burns, Valley Village, CA (US); Kyle Vos Strache, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 622 days.

(21) Appl. No.: 13/629,871

(22) Filed: Sep. 28, 2012

(65) Prior Publication Data
US 2017/0037422 A1    Feb. 9, 2017

Related U.S. Application Data

(60) Continuation-in-part of application No. 12/429,952, filed on Apr. 24, 2009, which is a continuation of application No. 10/953,349, filed on Sep. 30, 2004, now abandoned, application No. 13/629,871, which is a continuation-in-part of application No. 11/053,711, filed on Feb. 7, 2005, now abandoned, application No. 13/629,871, which is a continuation-in-part of application No. 12/924,927, filed on Oct. 8, 2010, now abandoned, which is a division of application No. 11/713,768, filed on Mar. 2, 2007, now abandoned, which is a continuation of application No. 11/056,355, filed on Feb. 14, 2005, now abandoned, application No. 13/629,871, which is a continuation-in-part of application No. 12/498,986, filed on Jul. 7, 2009, now abandoned, which is a continuation of application No. 11/096,568, filed on Apr. 1, 2005, now abandoned, application No. 13/629,871, which is a continuation-in-part of application No. 13/453,954, filed on Apr. 23, 2012, now abandoned, which is a division of application No. 12/974,661, filed on Dec. 21, 2010, now Pat. No. 8,183,436, which is a continuation of application No. 12/145,273, filed on Jun. 24, 2008, now abandoned, which is a continuation of application No. 11/649,663, filed on Jan. 3, 2007, now abandoned, which is a continuation of application No. 11/174,307, filed on Jun. 30, 2005, now abandoned, application No. 13/629,871, which is a continuation-in-part of application No. 13/474,296, filed on May 17, 2012, now abandoned, which is a division of application No. 12/435,281, filed on May 4, 2009, now abandoned, which is a continuation of application No. 11/241,607, filed on Sep. 30, 2005, now Pat. No. 7,569,389, application No. 13/629,871, which is a continuation-in-part of application No. 12/960,379, filed on Dec. 3, 2010, now abandoned, (Continued)

(51) Int. Cl.
| A01H 5/10 | (2006.01) |
| C12N 15/82 | (2006.01) |
| C07K 14/415 | (2006.01) |
| C12Q 1/68 | (2018.01) |

(52) U.S. Cl.
CPC ........ *C12N 15/8261* (2013.01); *C07K 14/415* (2013.01); *C12Q 1/6895* (2013.01)

(58) Field of Classification Search
None
See application file for complete search history.

(56) References Cited

U.S. PATENT DOCUMENTS 6,768,043 B2    7/2004   Chory et al.
7,109,033 B2    9/2006   Harper et al.
(Continued)

FOREIGN PATENT DOCUMENTS

EP         1 033 405 A2    9/2000
WO    WO 2003/008540 A2    1/2003
(Continued)

OTHER PUBLICATIONS

Guo et al (PNAS 2004 (101)25, 9205-9210).*
(Continued)

*Primary Examiner* — Lee A Visone
(74) *Attorney, Agent, or Firm* — Dentons US LLP

(57) ABSTRACT

The present invention provides DNA molecules that constitute fragments of the genome of a plant, and polypeptides encoded thereby. The DNA molecules are useful for specifying a gene product in cells, either as a promoter or as a protein coding sequence or as an UTR or as a 3' termination sequence, and are also useful in controlling the behavior of a gene in the chromosome, in controlling the expression of a gene or as tools for genetic mapping, recognizing or isolating identical or related DNA fragments, or identification of a particular individual organism, or for clustering of a group of organisms with a common trait.

13 Claims, 2 Drawing Sheets

Related U.S. Application Data which is a continuation of application No. 11/317,789, filed on Dec. 22, 2005, now abandoned, which is a continuation-in-part of application No. 11/241,673, filed on Sep. 30, 2005, now abandoned, application No. 13/629,871, which is a continuation-in-part of application No. 13/235,320, filed on Sep. 16, 2011, now abandoned, which is a continuation of application No. 11/787,902, filed on Apr. 17, 2007, now abandoned, application No. 13/629,871, which is a continuation-in-part of application No. 13/164,669, filed on Jun. 20, 2011, now abandoned, which is a division of application No. 11/897,944, filed on Aug. 31, 2007, now Pat. No. 7,989,676, application No. 13/629,871, which is a continuation-in-part of application No. 12/583,039, filed on Aug. 12, 2009, now Pat. No. 8,344,211.

(60) Provisional application No. 60/507,912, filed on Sep. 30, 2003, provisional application No. 60/542,691, filed on Feb. 6, 2004, provisional application No. 60/544,109, filed on Feb. 13, 2004, provisional application No. 60/558,095, filed on Apr. 1, 2004, provisional application No. 60/583,671, filed on Jun. 30, 2004, provisional application No. 60/583,781, filed on Jun. 30, 2004, provisional application No. 60/583,651, filed on Jun. 30, 2004, provisional application No. 60/615,270, filed on Sep. 30, 2004, provisional application No. 60/638,820, filed on Dec. 22, 2004, provisional application No. 60/637,210, filed on Dec. 16, 2004, provisional application No. 60/614,271, filed on Sep. 30, 2004, provisional application No. 60/614,332, filed on Sep. 30, 2004, provisional application No. 60/627,206, filed on Nov. 12, 2004, provisional application No. 60/639,228, filed on Dec. 22, 2004, provisional application No. 60/615,055, filed on Sep. 30, 2004, provisional application No. 60/792,722, filed on Apr. 17, 2006, provisional application No. 60/841,779, filed on Aug. 31, 2006, provisional application No. 61/188,944, filed on Aug. 13, 2008.

(56) References Cited

U.S. PATENT DOCUMENTS

| | | |
|---|---|---|
| 7,179,904 B2 | 2/2007 | Kwok |
| 7,238,860 B2 | 7/2007 | Ratcliffe et al. |
| 7,511,190 B2 | 3/2009 | Sherman et al. |
| 8,193,409 B2 | 6/2012 | Feldmann et al. |
| 2004/0031072 A1 | 2/2004 | La Rosa et al. |
| 2004/0034888 A1 | 2/2004 | Liu et al. |
| 2004/0123343 A1 | 6/2004 | La Rosa et al. |
| 2004/0214272 A1 | 10/2004 | La Rosa et al. |
| 2004/0216190 A1* | 10/2004 | Kovalic .............. C07H 21/04 800/289 |
| 2007/0283460 A9 | 12/2007 | Liu et al. |

FOREIGN PATENT DOCUMENTS

| | | |
|---|---|---|
| WO | WO 2003/013227 A2 | 2/2003 |
| WO | WO 2005/019462 A1 | 3/2005 |
| WO | WO 2006/004955 A2 | 1/2006 |
| WO | WO 2008/006033 A1 | 1/2008 |

OTHER PUBLICATIONS

GenBank Accession NP_001142794.1 (2009).*
GenBank Accession NM_001149322.1 (2009).*
Yanagisawa et al., "Involvement of Maize Dof Zinc Finger Proteins in Tissue-Specific and Light-Regulated Gene Expression," *The Plant Cell*; vol. 10; pp. 75-89; Jan. 1998.
Yanagisawa, "Dof Domain Proteins: Plant-specific Transcription factors associated with diverse phenomena unique to plants," *Plant Cell Physio*; 45(4) pp. 386-391; 2004.
U.S. Appl. No. 09/752,823, filed Jan. 3, 2001, Alexandrov et al.
Bock et al., "Taming plastids for a green future," *Trends in Biotechnology*, 22(6):311-318, 2004.
Bork et al., "Go hunting in sequence databases but watch out for the traps," *Trends in Genetics*, 12(10): 425-427, 1996.
Bowie et al., "Deciphering the message in protein sequences: tolerance to amino acid substitutions," *Science*, 247(4948)1306-1310, 1990.
Dai et al., "The rice YABBY1 gene is involved in the feedback of regulation of Gibberellin metabolism," *Plant Physiology*, 144:121-133, 2007.
Dewaele et al., "Metabolic engineering of a complex biochemical pathway: the lysine and threonine biosynthesis as an example," *Phytochemistry Reviews*, 1(1):125-133, 2002.
Doerks et al. "Protein annotation: detective work for function prediction," *Trends in Genetics*, 14: 248-250, 1998.
EMBL AY087999.1, "*Arabidopsis thaliana* clone 40252 mRNA, complete sequence."
Eriksson et al., "Increased gibberellin biosynthesis in transgenic trees promotes growth, biomass production and xylem fiber length," *Nature Biotechnology*, 18:784-788, 2000.
Guo et al., "Protein tolerance to random amino acid change," *Proc Natl Acad Sci U S A*, 101:9205-9210, 2004.
GenBank BAG91095.1, "unnamed protein product [*Oryza sativa* Japonica Group]."
GenBank CV267710.1, "WS02032.B21_H19 PTxNIBNA11 Populus trichocarpa x Populus nigra cDNA clone WS02032_H19 3, mRNA sequence."
GenBank XP_002440915, "hypothetical protein SORBIDRAFT_09g016440 [Sorghum bicolor]".
Hanzawa et al. "A single amino acid converts a repressor to an activator of flowering," *Proc Natl Acad Sci U S A*, 102:7748-7753, 2005.
Jaglo et al., "Components of the *Arabidopsis* C-repeat/dehydration-responsive element binding factor cold-response pathway are conserved in *Brassica napus* and other plant species," *Plant Physiology*, 127:910-917, 2001.
Jeanneau et al., "Manipulating PEPC levels in plants," *Journal of Experimental Botany*, 53(376):1837-1845, 2002.
Keskin et al., "A new, structurally nonredundant, diverse data set of protein-protein interfaces and its implications," *Protein Science*, 13:1043-1055, 2004.
McConnell et al., "Role of Phabulosa and Phavoluta in determining radial patterning in shoots," *Nature*, 411(6838):709-713, 2001.
Murphy, "Engineering oil production in rapeseed and other oil crops," *Trends in Biotechnology*, 14(6):206-213, 1996.
Nam, "The molecular genetic analysis of leaf senescence," *Current Opinion in Biotechnology*, 8(2); 200-207, 1997.
Ngo et al., "Computational Complexity, Protein Structure Prediction, and the Levinthal Paradox," *The Protein Folding Problem and Tertiary Structure Prediction*, 492-495, 1994.
Roy et al., "Arginine decarboxylase transgene expression and analysis of environmental stress tolerance in transgenic rice," *Plant Science*, 160:869-875, 2001.
Sinha et al., "Overexpression of the maize homeo box gene, KNOTTED-1, causes a switch from determinate to indeterminate cell fates," *Genes & Development*, 7:787-795, 1993.
Sivamani et al., "Improved biomass productivity and water use efficiency under water deficit conditions in transgenic wheat constitutively expressing the barley HVA1 gene," *Plant Science*, 155(1):1-9, 2000.
Smith et al., "The challenges of genome sequence annotation or 'The devil is in the details,'" *Nature Biotechnology*, 15:1222-1223, 1997.
Thornton et al., "From structure to function: approaches and limitations," *Nature Structural Biology*, Structural Genomics Supplement, 991-994, 2000.

(56) References Cited

OTHER PUBLICATIONS

UniProt Q8LA65, "Uncharacterized protein."
UniProt Q9LGS7, "Os01g0183600 protein."
Wells, "Additivity of mutational effects in proteins," *Biochemistry*, 29(37)8509-8517, 1990.
Zhao et al., "Overexpression of LSH1, a member of an uncharacterised gene family, causes enhanced light regulation of seedling development," *The Plant Journal*, 37: 694-706, 2004.

* cited by examiner

SEQUENCE DETERMINED DNA FRAGMENTS AND CORRESPONDING POLYPEPTIDES ENCODED THEREBY

CROSS REFERENCES TO RELATED APPLICATIONS

This application in a Continuation-in-Part of co-pending application Ser. No. 12/429,952 filed on Apr. 24, 2009 and for which priority is claimed under 35 U.S.C. § 120. Application Ser. No. 12/429,952 is a Continuation of application Ser. No. 10/953,349, now abandoned, filed on Sep. 30, 2004. Application Ser. No. 10/953,349 is a nonprovisional application which claims priority under 35 U.S.C. § 119(e) to U.S. Provisional Application No. 60/507,912 filed on Sep. 30, 2003, the entire contents of each of which are incorporated by reference, including their sequence listings.

This application in a Continuation-in-Part of co-pending application Ser. No. 11/053,711 filed on Feb. 7, 2005 and for which priority is claimed under 35 U.S.C. § 120. Application Ser. No. 11/053,711 is a nonprovisional application, which claims priority under 35 U.S.C. § 119(e) to U.S. Provisional Application No. 60/542,691 filed on Feb. 6, 2004, the entire contents of each of which are incorporated by reference, including their sequence listings.

This application in a Continuation-in-Part of co-pending application Ser. No. 12/924,927 filed on Oct. 8, 2010 and for which priority is claimed under 35 U.S.C. § 120. Application Ser. No. 12/924,927 is a Divisional of application Ser. No. 11/713,768, now abandoned, filed on Mar. 2, 2007. Application Ser. No. 11/713,768 is a Continuation of application Ser. No. 11/056,355, now abandoned, filed on Feb. 14, 2005, which claims priority under 35 U.S.C. § 119(e) to U.S. Provisional Application No. 60/544,190 filed on Feb. 13, 2004, the entire contents of each of which are incorporated by reference, including their sequence listings.

This application in a Continuation-in-Part of co-pending application Ser. No. 12/498,986 filed on Jul. 7, 2009 and for which priority is claimed under 35 U.S.C. § 120. Application Ser. No. 12/498,986 is a Continuation of application Ser. No. 11/096,568, now abandoned, filed on Apr. 1, 2005. Application Ser. No. 11/096,568 claims priority under 35 U.S.C. § 119(e) to U.S. Provisional Application No. 60/558,095 filed on Apr. 1, 2004, the entire contents of each of which are incorporated by reference, including their sequence listings.

This application is a Continuation-in-Part of co-pending application Ser. No. 13/453,954 filed on Apr. 23, 2012 and for which priority is claimed under 35 U.S.C. § 120. Application Ser. No. 13/453,954 is a Divisional of application Ser. No. 12/974,661, now U.S. Pat. No. 8,183,436, filed on Dec. 21, 2010, which is a Continuation of application Ser. No. 12/145,273, now abandoned, filed on Jun. 24, 2008, which is a Continuation of application Ser. No. 11/649,663, now abandoned, filed on Jan. 3, 2007, which is a Continuation of application Ser. No. 11/174,307, now abandoned, filed on Jun. 30, 2005. Application Ser. No. 11/174,307 claims priority under 35 U.S.C. § 119(e) to U.S. Provisional Application Nos. 60/583,671; 60/583,781 and 60/583,651, all filed on Jun. 30, 2004; the entire contents of each of which are hereby incorporated by reference including their sequence listings.

This application is a Continuation-in-Part of co-pending application Ser. No. 13/474,296 filed on May 17, 2012 and for which priority is claimed under 35 U.S.C. § 120. Application Ser. No. 13/474,296 is a Divisional of application Ser. No. 12/435,281, now abandoned, filed on May 4, 2009, which is a Continuation of application Ser. No. 11/241,607, now U.S. Pat. No. 7,569,389, filed on Sep. 30, 2005. Application Ser. No. 11/241,607 claims priority under 35 U.S.C. § 119(e) to U.S. Provisional Application Nos. 60/615,270 filed on Sep. 30, 2004, 60/638,820 filed on Dec. 22, 2004, 60/637,210 filed on Dec. 16, 2004, 60/614,271 filed on Sep. 30, 2004, 60/614,332 filed on Sep. 30, 2004 and 60/627,206 filed on Nov. 12, 2004, the entire contents of each of which are hereby incorporated by reference including their sequence listings.

This application in a Continuation-in-Part of co-pending application Ser. No. 12/960,379 filed on Dec. 3, 2010 and for which priority is claimed under 35 U.S.C. § 120. Application Ser. No. 12/960,379 is a Continuation of application Ser. No. 11/317,789, now abandoned, filed on Dec. 22, 2005. Application Ser. No. 11/317,789 is a Continuation-in-Part of application Ser. No. 11/241,673, now abandoned, filed on Sep. 30, 2005. Application Ser. No. 11/241,673 claims priority under 35 U.S.C. § 119(e) to U.S. Provisional Application Nos. 60/639,228 filed on Dec. 22, 2004, and 60/615,055, filed on Sep. 30, 2004, the entire contents of each of which are incorporated by reference, including their sequence listings.

This application in a Continuation-in-Part of co-pending application Ser. No. 13/235,320 filed on Sep. 16, 2011 and for which priority is claimed under 35 U.S.C. § 120. Application Ser. No. 13/235,320 is a Continuation of application Ser. No. 11/787,902, now abandoned, filed on Apr. 17, 2007. Application Ser. No. 11/787,902 claims priority under 35 U.S.C. § 119(e) to U.S. Provisional Application No. 60/792,722 filed on Apr. 17, 2006, the entire contents of each of which are incorporated by reference, including their sequence listings.

This application in a Continuation-in-Part of co-pending application Ser. No. 13/164,669 filed on Jun. 20, 2011 and for which priority is claimed under 35 U.S.C. § 120. Application Ser. No. 13/164,669 is a Divisional of application Ser. No. 11/897,944, now U.S. Pat. No. 7,989,676, filed on Aug. 31, 2007. Application Ser. No. 11/897,944 claims priority under 35 U.S.C. § 119(e) to U.S. Provisional Application No. 60/841,779 filed on Aug. 31, 2006, the entire contents of each of which are incorporated by reference, including their sequence listings.

This application in a Continuation-in-Part of co-pending application Ser. No. 12/583,039 filed on Aug. 12, 2009 and for which priority is claimed under 35 U.S.C. § 120. Application Ser. No. 12/583,039 is a nonprovisional application which claims priority under 35 U.S.C. § 119(e) to U.S. Provisional Application No. 61/188,944 filed on Aug. 13, 2008, the entire contents of each of which are incorporated by reference, including their sequence listings.

FIELD OF THE INVENTION

The present invention relates to isolated polynucleotides that represent a complete gene, or a fragment thereof, that is expressed. In addition, the present invention relates to the polypeptide or protein corresponding to the coding sequence of these polynucleotides. The present invention also relates to isolated polynucleotides that represent regulatory regions of genes. The present invention also relates to isolated polynucleotides that represent untranslated regions of genes. The present invention further relates to the use of these isolated polynucleotides and polypeptides and proteins.

DESCRIPTION OF THE RELATED ART

Efforts to map and sequence the genome of a number of organisms are in progress; a few complete genome sequences, for example those of *E. coli* and *Saccharomyces cerevisiae* are known (Blattner et al., *Science* 277:1453 (1997); Goffeau et al., *Science* 274:546 (1996)). The complete genome of a multicellular organism, *C. elegans*, has also been sequenced (See, the *C. elegans* Sequencing Consortium, *Science* 282:2012 (1998)).

SUMMARY OF THE INVENTION

The present invention comprises polynucleotides, such as complete cDNA sequences and/or sequences of genomic DNA encompassing complete genes, fragments of genes, and/or regulatory elements of genes and/or regions with other functions and/or intergenic regions, hereinafter collectively referred to as Sequence-Determined DNA Fragments (SDFs), from different plant species, particularly corn, wheat, soybean, rice and *Arabidopsis thaliana*, and other plants and or mutants, variants, fragments or fusions of said SDFs and polypeptides or proteins derived therefrom. In some instances, the SDFs span the entirety of a protein-coding segment. In some instances, the entirety of an mRNA is represented. Other objects of the invention that are also represented by SDFs of the invention are control sequences, such as, but not limited to, promoters. Complements of any sequence of the invention are also considered part of the invention.

Other objects of the invention are polynucleotides comprising exon sequences, polynucleotides comprising intron sequences, polynucleotides comprising introns together with exons, intron/exon junction sequences, 5' untranslated sequences, and 3' untranslated sequences of the SDFs of the present invention. Polynucleotides representing the joinder of any exons described herein, in any arrangement, for example, to produce a sequence encoding any desirable amino acid sequence are within the scope of the invention.

The present invention also resides in probes useful for isolating and identifying nucleic acids that hybridize to an SDF of the invention. The probes can be of any length, but more typically are 12-2000 nucleotides in length; more typically, 15 to 200 nucleotides long; even more typically, 18 to 100 nucleotides long.

Yet another object of the invention is a method of isolating and/or identifying nucleic acids using the following steps:

(a) contacting a probe of the instant invention with a polynucleotide sample under conditions that permit hybridization and formation of a polynucleotide duplex; and (b) detecting and/or isolating the duplex of step (a).

The conditions for hybridization can be from low to moderate to high stringency conditions. The sample can include a polynucleotide having a sequence unique in a plant genome. Probes and methods of the invention are useful, for example, without limitation, for mapping of genetic traits and/or for positional cloning of a desired fragment of genomic DNA.

Probes and methods of the invention can also be used for detecting alternatively spliced messages within a species. Probes and methods of the invention can further be used to detect or isolate related genes in other plant species using genomic DNA (gDNA) and/or cDNA libraries. In some instances, especially when longer probes and low to moderate stringency hybridization conditions are used; the probe will hybridize to a plurality of cDNA and/or gDNA sequences of a plant. This approach is useful for isolating representatives of gene families which are identifiable by possession of a common functional domain in the gene product or which have common cis-acting regulatory sequences. This approach is also useful for identifying orthologous genes from other organisms.

The present invention also resides in constructs for modulating the expression of the genes comprised of all or a fragment of an SDF. The constructs comprise all or a fragment of the expressed SDF, or of a complementary sequence. Examples of constructs include ribozymes comprising RNA encoded by an SDF or by a sequence complementary thereto, antisense constructs, constructs comprising coding regions or parts thereof, constructs comprising promoters, introns, untranslated regions, scaffold attachment regions, methylating regions, enhancing or reducing regions, DNA and chromatin conformation modifying sequences, etc. Such constructs can be constructed using viral, plasmid, bacterial artificial chromosomes (BACs), plasmid artificial chromosomes (PACs), autonomous plant plasmids, plant artificial chromosomes or other types of vectors and exist in the plant as autonomous replicating sequences or as DNA integrated into the genome. When inserted into a host cell the construct is, preferably, functionally integrated with, or operatively linked to, a heterologous polynucleotide. For instance, a coding region from an SDF might be operably linked to a promoter that is functional in a plant.

The present invention also resides in host cells, including bacterial or yeast cells or plant cells, and plants that harbor constructs such as described above. Another aspect of the invention relates to methods for modulating expression of specific genes in plants by expression of the coding sequence of the constructs, by regulation of expression of one or more endogenous genes in a plant or by suppression of expression of the polynucleotides of the invention in a plant. Methods of modulation of gene expression include without limitation (1) inserting into a host cell additional copies of a polynucleotide comprising a coding sequence; (2) modulating an endogenous promoter in a host cell; (3) inserting antisense or ribozyme constructs into a host cell and (4) inserting into a host cell a polynucleotide comprising a sequence encoding a variant, fragment, or fusion of the native polypeptides of the instant invention.

BRIEF DESCRIPTION OF THE TABLES

The sequences of exemplary SDFs and polypeptides corresponding to the coding sequences of the instant invention are described in any of the Reference Tables 1-1, 1-2, etc. (hereinafter referred to as "the REF Tables"); and in any of the Sequence Tables 2-1, 2-2, etc. (hereinafter referred to as "the SEQ Tables"). The REF Tables refer to a number of "Maximum Length Sequences" or "MLS." Each MLS corresponds to the longest cDNA obtained, either by cloning or by the prediction from genomic sequence. The sequence of the MLS is the cDNA sequence as described in the Av subsection of the REF Tables.

The REF Tables include the following information relating to each MLS:

I. cDNA Sequence
  A. 5' UTR
  B. Coding Sequence
  C. 3' UTR
II. Genomic Sequence
  A. Exons
  B. Introns
  C. Promoters
III. Link of cDNA Sequences to Clone IDs
IV. Multiple Transcription Start Sites
V. Polypeptide Sequences
  A. Signal Peptide
  B. Domains
  C. Related Polypeptides
VI. Related Polynucleotide Sequences I. cDNA Sequence The REF Tables indicate which sequence in The SEQ Tables represent the sequence of each MLS. The MLS sequence can comprise 5' and 3' UTR as well as coding sequences. In addition, specific cDNA clone numbers also are included in The REF Tables when the MLS sequence relates to a specific cDNA clone.

A. 5' UTR

The location of the 5' UTR can be determined by comparing the most 5' MLS sequence with the corresponding genomic sequence as indicated in The REF Tables. The sequence that matches, beginning at any of the transcriptional start sites and ending at the last nucleotide before any of the translational start sites corresponds to the 5' UTR.

B. Coding Region

The coding region is the sequence in any open reading frame found in the MLS. Coding regions of interest are indicated in the PolyP SEQ subsection of The REF Tables.

C. 3' UTR

The location of the 3' UTR can be determined by comparing the most 3' MLS sequence with the corresponding genomic sequence as indicated in The REF Tables. The sequence that matches, beginning at the translational stop site and ending at the last nucleotide of the MLS corresponds to the 3' UTR.

II. Genomic Sequence

Figure 2:
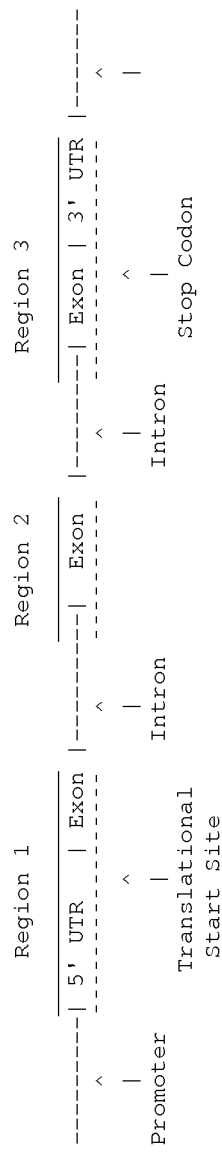
FIG. 2 presents the typical orientation of the promoter, 5' and 3' UTRs, translational start site, exons, introns and stop codon.

Further, the REF Tables indicate the specific "gi" number of the genomic sequence if the sequence resides in a public databank. For each genomic sequence, the REF Tables indicate which regions are included in the MLS. These regions can include the 5' and 3' UTRs as well as the coding sequence of the MLS. See, for example, FIG. 2.

The REF Tables report the first and last base of each region that are included in an MLS sequence. An example is shown below:

gi No. 47000:
  37102 . . . 37497
  37593 . . . 37925

The numbers indicate that the MLS contains the following sequences from two regions of gi No. 47000; a first region including bases 37102-37497, and a second region including bases 37593-37925.

A. Exon Sequences

The location of the exons can be determined by comparing the sequence of the regions from the genomic sequences with the corresponding MLS sequence as indicated by the REF Tables.

i. Initial Exon

To determine the location of the initial exon, information from the
  (1) polypeptide sequence section;
  (2) cDNA polynucleotide section; and
  (3) the genomic sequence section
of the REF Tables are used. First, the polypeptide section will indicate where the translational start site is located in the MLS sequence. The MLS sequence can be matched to the genomic sequence that corresponds to the MLS. Based on the match between the MLS and corresponding genomic sequences, the location of the translational start site can be determined in one of the regions of the genomic sequence. The location of this translational start site is the start of the first exon.

Generally, the last base of the exon of the corresponding genomic region, in which the translational start site was located, will represent the end of the initial exon. In some cases, the initial exon will end with a stop codon, when the initial exon is the only exon.

In the case when sequences representing the MLS are in the positive strand of the corresponding genomic sequence, the last base will be a larger number than the first base. When the sequences representing the MLS are in the negative strand of the corresponding genomic sequence, then the last base will be a smaller number than the first base.

ii. Internal Exons

Except for the regions that comprise the 5' and 3' UTRs, initial exon, and terminal exon, the remaining genomic regions that match the MLS sequence are the internal exons. Specifically, the bases defining the boundaries of the remaining regions also define the intron/exon junctions of the internal exons.

iii. Terminal Exon

As with the initial exon, the location of the terminal exon is determined with information from the
  (1) polypeptide sequence section;
  (2) cDNA polynucleotide section; and
  (3) the genomic sequence section
of the REF Tables. The polypeptide section will indicate where the stop codon is located in the MLS sequence. The MLS sequence can be matched to the corresponding genomic sequence. Based on the match between MLS and corresponding genomic sequences, the location of the stop codon can be determined in one of the regions of the genomic sequence. The location of this stop codon is the end of the terminal exon. Generally, the first base of the exon of the corresponding genomic region that matches the cDNA sequence, in which the stop codon was located, will represent the beginning of the terminal exon. In some cases, the translational start site will represent the start of the terminal exon, which will be the only exon.

In the case when the MLS sequences are in the positive strand of the corresponding genomic sequence, the last base will be a larger number than the first base. When the MLS sequences are in the negative strand of the corresponding genomic sequence, then the last base will be a smaller number than the first base.

B. Intron Sequences

In addition, the introns corresponding to the MLS are defined by identifying the genomic sequence located between the regions where the genomic sequence comprises exons. Thus, introns are defined as starting one base downstream of a genomic region comprising an exon, and end one base upstream from a genomic region comprising an exon.

C. Promoter Sequences

As indicated below, promoter sequences corresponding to the MLS are defined as sequences upstream of the first exon; more usually, as sequences upstream of the first of multiple transcription start sites; even more usually as sequences about 2,000 nucleotides upstream of the first of multiple transcription start sites.

III. Link of cDNA Sequences to Clone IDs

As noted above, the REF Tables identify the cDNA clone(s) that relate to each MLS. The MLS sequence can be longer than the sequences included in the cDNA clones. In such a case, the REF Tables indicate the region of the MLS that is included in the clone. If either the 5' or 3' termini of the cDNA clone sequence is the same as the MLS sequence, no mention will be made.

IV. Multiple Transcription Start Sites

Initiation of transcription can occur at a number of sites of the gene. The REF Tables indicate the possible multiple transcription sites for each gene. In the REF Tables, the location of the transcription start sites can be either a positive or negative number. The positions indicated by positive numbers refer to the transcription start sites as located in the MLS sequence. The negative numbers indicate the transcription start site within the genomic sequence that corresponds to the MLS.

To determine the location of the transcription start sites with the negative numbers, the MLS sequence is aligned with the corresponding genomic sequence. In the instances when a public genomic sequence is referenced, the relevant corresponding genomic sequence can be found by direct reference to the nucleotide sequence indicated by the "gi" number shown in the public genomic DNA section of the REF Tables. When the position is a negative number, the transcription start site is located in the corresponding genomic sequence upstream of the base that matches the beginning of the MLS sequence in the alignment. The negative number is relative to the first base of the MLS sequence which matches the genomic sequence corresponding to the relevant "gi" number.

In the instances when no public genomic DNA is referenced, the relevant nucleotide sequence for alignment is the nucleotide sequence associated with the amino acid sequence designated by "gi" number of the later PolyP SEQ subsection.

V. Polypeptide Sequences

The PolyP SEQ subsection lists SEQ ID NOs and Ceres SEQ ID NO for polypeptide sequences corresponding to the coding sequence of the MLS sequence and the location of the translational start site with the coding sequence of the MLS sequence.

The MLS sequence can have multiple translational start sites and can be capable of producing more than one polypeptide sequence.

A. Signal Peptide

The REF Tables also indicate in subsection (B) the cleavage site of the putative signal peptide of the polypeptide corresponding to the coding sequence of the MLS sequence. Typically, signal peptide coding sequences comprise a sequence encoding the first residue of the polypeptide to the cleavage site residue.

B. Domains

Subsection (C) provides information regarding identified domains (where present) within the polypeptide and (where present) a name for the polypeptide domain.

C. Related Polypeptides

Subsection (Dp) provides (where present) information concerning amino acid sequences that are found to be related and have some percentage of sequence identity to the polypeptide sequences of the REF Tables and the SEQ Tables. These related sequences are identified by a "gi" number.

VI. Related Polynucleotide Sequences

Subsection (Dn) provides polynucleotide sequences (where present) that are related to and have some percentage of sequence identity to the MLS or corresponding genomic sequence.

| Abbreviation | Description |
| --- | --- |
| Max Len. Seq. | Maximum Length Sequence |
| rel to | Related to |
| Clone Ids | Clone ID numbers |
| Pub gDNA | Public Genomic DNA |
| gi No. | gi number |
| Gen. Seq. in cDNA | Genomic Sequence in cDNA (Each region for a single gene prediction is listed on a separate line. In the case of multiple gene predictions, the group of regions relating to a single prediction are separated by a blank line) |
| (Ac) cDNA SEQ | cDNA sequence |
| Pat. Appln. SEQ ID NO | Patent Application SEQ ID NO: |
| Ceres SEQ ID NO: 1673877 | Ceres SEQ ID NO: |
| SEQ # w. TSS | Location within the cDNA sequence, SEQ ID NO:, of Transcription Start Sites which are listed below |
| Clone ID #: # -> # | Clone ID comprises bases # to # of the cDNA Sequence |
| PolyP SEQ | Polypeptide Sequence |
| Pat. Appln. SEQ ID NO: | Patent Application SEQ ID NO: |
| Ceres SEQ ID NO | Ceres SEQ ID NO: |
| Loc. SEQ ID NO: @ nt. | Location of translational start site in cDNA of SEQ ID NO: at nucleotide number |
| (C) Pred. PP Nom. & Annot. (Title) | Nomination and Annotation of Domains within Predicted Polypeptide(s) Name of Domain |
| Loc. SEQ ID NO #: # -> # aa. | Location of the domain within the polypeptide of SEQ ID NO: from # to # amino acid residues. |
| (Dp) Rel. AA SEQ | Related Amino Acid Sequences |
| Align. NO | Alignment number |
| gi No | Gi number |
| Desp. | Description |
| % Idnt. | Percent identity |
| Align. Len. | Alignment Length |
| Loc. SEQ ID NO: # -> # aa | Location within SEQ ID NO: from # to # amino acid residue. |

DETAILED DESCRIPTION OF THE INVENTION

The invention relates to (I) polynucleotides and methods of use thereof, such as IA. Probes, Primers and Substrates;
IB. Methods of Detection and Isolation;
B.1. Hybridization;
B.2. Methods of Mapping;
B.3. Southern Blotting;
B.4. Isolating cDNA from Related Organisms;
B.5. Isolating and/or Identifying Orthologous Genes
IC. Methods of Inhibiting Gene Expression
C.1. Antisense
C.2. Ribozyme Constructs;
C.3. Chimeraplasts;
C.4 Co-Suppression;
C.5. Transcriptional Silencing
C.6. Other Methods to Inhibit Gene Expression
ID. Methods of Functional Analysis;
IE. Promoter Sequences and Their Use;
IF. UTRs and/or Intron Sequences and Their Use; and
IG. Coding Sequences and Their Use.

The invention also relates to (II) polypeptides and proteins and methods of use thereof, such as IIA. Native Polypeptides and Proteins
A.1 Antibodies
A.2 In Vitro Applications
IIB. Polypeptide Variants, Fragments and Fusions
B.1 Variants
B.2 Fragments
B.3 Fusions The invention also includes (III) methods of modulating polypeptide production, such as IIIA. Suppression
A.1 Antisense
A.2 Ribozymes
A.3 Co-suppression
A.4 Insertion of Sequences into the Gene to be Modulated
A.5 Promoter Modulation
A.6 Expression of Genes containing Dominant-Negative Mutations
IIIB. Enhanced Expression
B.1 Insertion of an Exogenous Gene
B.2 Promoter Modulation The invention further concerns (IV) gene constructs and vector construction, such as IVA. Coding Sequences
IVB. Promoters
IVC. Signal Peptides The invention still further relates to V Transformation Techniques

DEFINITIONS

Allelic variant: An "allelic variant" is an alternative form of the same SDF, which resides at the same chromosomal locus in the organism. Allelic variations can occur in any portion of the gene sequence, including regulatory regions. Allelic variants can arise by normal genetic variation in a population. Allelic variants can also be produced by genetic engineering methods. An allelic variant can be one that is found in a naturally occurring plant, including a cultivar or ecotype. An allelic variant may or may not give rise to a phenotypic change, and may or may not be expressed. An allele can result in a detectable change in the phenotype of the trait represented by the locus. A phenotypically silent allele can give rise to a product.

Alternatively spliced messages: Within the context of the current invention, "alternatively spliced messages" refers to mature mRNAs originating from a single gene with variations in the number and/or identity of exons, introns and/or intron-exon junctions.

Chimeric: The term "chimeric" is used to describe genes, as defined supra, or constructs wherein at least two of the elements of the gene or construct, such as the promoter and the coding sequence and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Coordinately Expressed: The term "coordinately expressed," as used in the current invention, refers to genes that are expressed at the same or a similar time and/or stage and/or under the same or similar environmental conditions.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Filler sequence: As used herein, "filler sequence" refers to any nucleotide sequence that is inserted into DNA construct to evoke a particular spacing between particular components such as a promoter and a coding region and may provide an additional attribute such as a restriction enzyme site.

Figure 1:
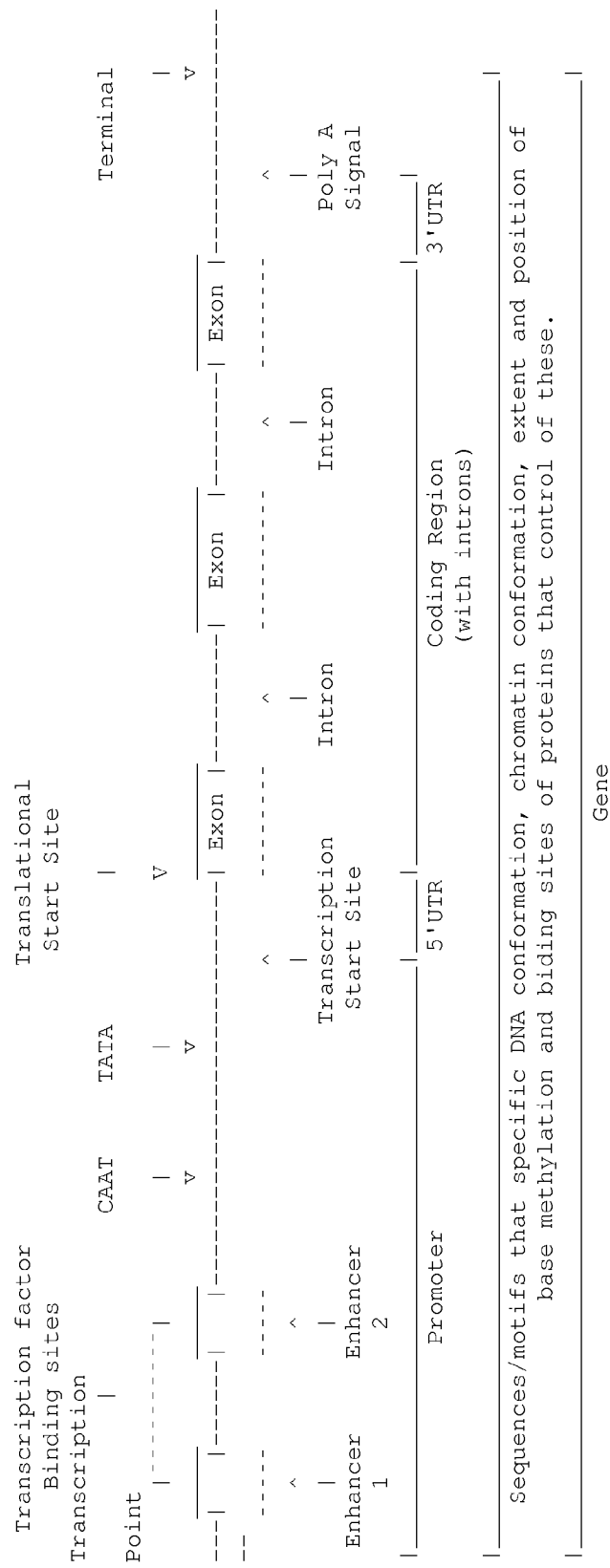
FIG. 1 presents a schematic of the components of a typical gene.

Gene: The term "gene," as used in the context of the current invention, encompasses all regulatory and coding sequence contiguously associated with a single hereditary unit with a genetic function (see FIG. 1). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes comprised of "exons" (coding sequences), which may be interrupted by "introns" (non-coding sequences), encode proteins. A gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, artificial chromosome, plasmid, vector, etc., or as a separate isolated entity.

Gene Family: "Gene family" is used in the current invention to describe a group of functionally related genes, each of which encodes a separate protein.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous gene: In the current invention, "homologous gene" refers to a gene that shares sequence similarity with the gene of interest. This similarity may be in only a fragment of the sequence and often represents a functional domain such as, examples including without limitation a DNA binding domain, a domain with tyrosine kinase activity, or the like. The functional activities of homologous genes are not necessarily the same.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, Plant J. 8:37 (1995)) Examples of environmental conditions that may affect transcription by inducible promoters include anaerobic conditions, elevated temperature, or the presence of light.

Intergenic region: "Intergenic region," as used in the current invention, refers to nucleotide sequence occurring in the genome that separates adjacent genes.

Mutant gene: In the current invention, "mutant" refers to a heritable change in DNA sequence at a specific location. Mutants of the current invention may or may not have an associated identifiable function when the mutant gene is transcribed.

Orthologous Gene: In the current invention "orthologous gene" refers to a second gene that encodes a gene product that performs a similar function as the product of a first gene. The orthologous gene may also have a degree of sequence similarity to the first gene. The orthologous gene may encode a polypeptide that exhibits a degree of sequence similarity to a polypeptide corresponding to a first gene. The sequence similarity can be found within a functional domain or along the entire length of the coding sequence of the genes and/or their corresponding polypeptides.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Plant Promoter: A "plant promoter" is a promoter capable of initiating transcription in plant cells and can drive or facilitate transcription of a fragment of the SDF of the instant invention or a coding sequence of the SDF of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1)promoter known to those of skill.

Promoter: The term "promoter," as used herein, refers to a region of sequence determinants located upstream from the start of transcription of a gene and which are involved in recognition and binding of RNA polymerase and other proteins to initiate and modulate transcription. A basal promoter is the minimal sequence necessary for assembly of a transcription complex required for transcription initiation. Basal promoters frequently include a "TATA box" element usually located between 15 and 35 nucleotides upstream from the site of initiation of transcription. Basal promoters also sometimes include a "CCAAT box" element (typically a sequence CCAAT) and/or a GGGCG sequence, usually located between 40 and 200 nucleotides, preferably 60 to 120 nucleotides, upstream from the start site of transcription.

Public sequence: The term "public sequence," as used in the context of the instant application, refers to any sequence that has been deposited in a publicly accessible database. This term encompasses both amino acid and nucleotide sequences. Such sequences are publicly accessible, for example, on the BLAST databases on the NCBI FTP web site (accessible at ncbi.nlm.gov/blast). The database at the NCBI GTP site utilizes "gi" numbers assigned by NCBI as a unique identifier for each sequence in the databases, thereby providing a non-redundant database for sequence from various databases, including GENBANK, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and rate, and stability and/or mobility of the transcript or polypeptide product. Regulatory sequences include, but are not limited to, promoters, promoter control elements, protein binding sequences, 5' and 3' UTRs, transcriptional start site, termination sequence, polyadenylation sequence, introns, certain sequences within a coding sequence, etc.

Related Sequences: "Related sequences" refer to either a polypeptide or a nucleotide sequence that exhibits some degree of sequence similarity with a sequence described by the REF Tables and the SEQ Tables.

Scaffold Attachment Region (SAR): As used herein, "scaffold attachment region" is a DNA sequence that anchors chromatin to the nuclear matrix or scaffold to generate loop domains that can have either a transcriptionally active or inactive structure (Spiker and Thompson (1996) Plant Physiol. 110: 15-21).

Sequence-determined DNA fragments (SDFs): "Sequence-determined DNA fragments" as used in the current invention are isolated sequences of genes, fragments of genes, intergenic regions or contiguous DNA from plant genomic DNA or cDNA or RNA the sequence of which has been determined.

Signal Peptide: A "signal peptide" as used in the current invention is an amino acid sequence that targets the protein for secretion, for transport to an intracellular compartment or organelle or for incorporation into a membrane. Signal peptides are indicated in the tables and a more detailed description located below.

Specific Promoter: In the context of the current invention, "specific promoters" refers to a subset of inducible promoters that have a high preference for being induced in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: PTA29, a promoter which is capable of driving gene transcription specifically in tapetum and only during anther development (Koltonow et al., *Plant Cell* 2:1201 (1990); RCc2 and RCc3, promoters that direct root-specific gene transcription in rice (Xu et al., *Plant Mol. Biol.* 27:237 (1995); TobRB27, a root-specific promoter from tobacco (Yamamoto et al., *Plant Cell* 3:371 (1991)). Examples of tissue-specific promoters under developmental control include promoters that initiate transcription only in certain tissues or organs, such as root, ovule, fruit, seeds, or flowers. Other suitable promoters include those from genes encoding storage proteins or the lipid body membrane protein, oleosin. A few root-specific promoters are noted above.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% \text{ G+C})-(600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m=81.5+16.6 \log \{[Na^+]/(1+0.7[Na^+])\}+0.41(\% \text{ G+C})-500/L\ 0.63(\% \text{ formamide}) \quad (2)$$

where L is the length of the probe in the hybrid. (P. Tijessen, "Hybridization with Nucleic Acid Probes" in *Laboratory Techniques in Biochemistry and Molecular Biology*, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

Translational start site: In the context of the current invention, a "translational start site" is usually an ATG in the cDNA transcript, more usually the first ATG. A single cDNA, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

Untranslated region (UTR): A "UTR" is any contiguous series of nucleotide bases that is transcribed, but is not translated. These untranslated regions may be associated with particular functions such as increasing mRNA message stability. Examples of UTRs include, but are not limited to polyadenylation signals, terminations sequences, sequences located between the transcriptional start site and the first exon (5' UTR) and sequences located between the last exon and the end of the mRNA (3' UTR).

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc).

DETAILED DESCRIPTION OF THE INVENTION

I. Polynucleotides

Exemplified SDFs of the invention represent fragments of the genome of corn, wheat, rice, soybean or *Arabidopsis* and/or represent mRNA expressed from that genome. The isolated nucleic acid of the invention also encompasses corresponding fragments of the genome and/or cDNA complement of other organisms as described in detail below.

Polynucleotides of the invention can be isolated from polynucleotide libraries using primers comprising sequence similar to those described by the REF Tables and the SEQ Tables. See, for example, the methods described in Sambrook et al., supra.

Alternatively, the polynucleotides of the invention can be produced by chemical synthesis. Such synthesis methods are described below.

It is contemplated that the nucleotide sequences presented herein may contain some small percentage of errors. These errors may arise in the normal course of determination of nucleotide sequences. Sequence errors can be corrected by obtaining seeds deposited under the accession numbers cited above, propagating them, isolating genomic DNA or appropriate mRNA from the resulting plants or seeds thereof, amplifying the relevant fragment of the genomic DNA or mRNA using primers having a sequence that flanks the erroneous sequence, and sequencing the amplification product.

I.A. Probes, Primers and Substrates

SDFs of the invention can be applied to substrates for use in array applications such as, but not limited to, assays of global gene expression, for example under varying conditions of development, growth conditions. The arrays can also be used in diagnostic or forensic methods (WO95/35505, U.S. Pat. No. 5,445,943 and U.S. Pat. No. 5,410,270).

Probes and primers of the instant invention will hybridize to a polynucleotide comprising a sequence in the REF Tables and the SEQ Tables. Though many different nucleotide sequences can encode an amino acid sequence, the sequences of the REF Tables and the SEQ Tables are generally preferred for encoding polypeptides of the invention. However, the sequence of the probes and/or primers of the instant invention need not be identical to those in the REF Tables and the SEQ Tables or the complements thereof. For example, some variation in probe or primer sequence and/or length can allow additional family members to be detected, as well as orthologous genes and more taxonomically distant related sequences. Similarly, probes and/or primers of the invention can include additional nucleotides that serve as a label for detecting the formed duplex or for subsequent cloning purposes.

Probe length will vary depending on the application. For use as primers, probes are 12-40 nucleotides, preferably 18-30 nucleotides long. For use in mapping, probes are preferably 50 to 500 nucleotides, preferably 100-250 nucleotides long. For Southern hybridizations, probes as long as several kilobases can be used as explained below.

The probes and/or primers can be produced by synthetic procedures such as the triester method of Matteucci et al. *J. Am. Chem. Soc.* 103:3185 (1981); or according to Urdea et al. *Proc. Natl. Acad.* 80:7461 (1981) or using commercially available automated oligonucleotide synthesizers.

I.B. Methods of Detection and Isolation

The polynucleotides of the invention can be utilized in a number of methods known to those skilled in the art as probes and/or primers to isolate and detect polynucleotides, including, without limitation: Southerns, Northerns, Branched DNA hybridization assays, polymerase chain reaction, and microarray assays, and variations thereof. Specific methods given by way of examples, and discussed below include:

Hybridization
Methods of Mapping
Southern Blotting
Isolating cDNA from Related Organisms
Isolating and/or Identifying Orthologous Genes.

Also, the nucleic acid molecules of the invention can used in other methods, such as high density oligonucleotide hybridizing assays, described, for example, in U.S. Pat. Nos. 6,004,753; 5,945,306; 5,945,287; 5,945,308; 5,919,686; 5,919,661; 5,919,627; 5,874,248; 5,871,973; 5,871,971; and 5,871,930; and PCT Pub. Nos. WO 9946380; WO 9933981; WO 9933870; WO 9931252; WO 9915658; WO 9906572; WO 9858052; WO 9958672; and WO 9810858.

B.1. Hybridization

The isolated SDFs of the REF Tables and the SEQ Tables of the present invention can be used as probes and/or primers for detection and/or isolation of related polynucleotide sequences through hybridization. Hybridization of one nucleic acid to another constitutes a physical property that defines the subject SDF of the invention and the identified related sequences. Also, such hybridization imposes structural limitations on the pair. A good general discussion of the factors for determining hybridization conditions is provided by Sambrook et al. ("Molecular Cloning, a Laboratory Manual, 2nd ed., c. 1989 by Cold Spring Harbor Laboratory Press, Cold Spring Harbor, N.Y.; see esp., chapters 11 and 12). Additional considerations and details of the physical chemistry of hybridization are provided by G. H. Keller and M. M. Manak "DNA Probes", $2^{nd}$ Ed. pp. 1-25, c. 1993 by Stockton Press, New York, N.Y.

Depending on the stringency of the conditions under which these probes and/or primers are used, polynucleotides exhibiting a wide range of similarity to those in the REF and SEQ Tables can be detected or isolated. When the practitioner wishes to examine the result of membrane hybridizations under a variety of stringencies, an efficient way to do so is to perform the hybridization under a low stringency condition, then to wash the hybridization membrane under increasingly stringent conditions.

When using SDFs to identify orthologous genes in other species, the practitioner will preferably adjust the amount of target DNA of each species so that, as nearly as is practical, the same number of genome equivalents are present for each species examined. This prevents faint signals from species having large genomes, and thus small numbers of genome equivalents per mass of DNA, from erroneously being interpreted as absence of the corresponding gene in the genome.

The probes and/or primers of the instant invention can also be used to detect or isolate nucleotides that are "identical" to the probes or primers. Two nucleic acid sequences or polypeptides are said to be "identical" if the sequence of nucleotides or amino acid residues, respectively, in the two sequences is the same when aligned for maximum correspondence as described below.

Isolated polynucleotides within the scope of the invention also include allelic variants of the specific sequences presented in the REF and SEQ Tables. The probes and/or primers of the invention can also be used to detect and/or isolate polynucleotides exhibiting at least 80% sequence identity with the sequences of the REF and SEQ Tables or fragments thereof.

With respect to nucleotide sequences, degeneracy of the genetic code provides the possibility to substitute at least one base of the base sequence of a gene with a different base without causing the amino acid sequence of the polypeptide produced from the gene to be changed. Hence, the DNA of the present invention may also have any base sequence that has been changed from a sequence in the REF and SEQ Tables by substitution in accordance with degeneracy of genetic code. References describing codon usage include: Carels et al., *J. Mol. Evol.* 46: 45 (1998) and Fennoy et al., *Nucl. Acids Res.* 21(23): 5294 (1993).

B.2. Mapping

The isolated SDF DNA of the invention can be used to create various types of genetic and physical maps of the genome of corn, *Arabidopsis*, soybean, rice, wheat, or other plants. Some SDFs may be absolutely associated with particular phenotypic traits, allowing construction of gross genetic maps. While not all SDFs will immediately be associated with a phenotype, all SDFs can be used as probes for identifying polymorphisms associated with phenotypes of interest. Briefly, one method of mapping involves total DNA isolation from individuals. It is subsequently cleaved with one or more restriction enzymes, separated according to mass, transferred to a solid support, hybridized with SDF DNA and the pattern of fragments compared. Polymorphisms associated with a particular SDF are visualized as differences in the size of fragments produced between individual DNA samples after digestion with a particular restriction enzyme and hybridization with the SDF. After identification of polymorphic SDF sequences, linkage studies can be conducted. By using the individuals showing polymorphisms as parents in crossing programs, F2 progeny recombinants or recombinant inbreds, for example, are then analyzed. The order of DNA polymorphisms along the chromosomes can be determined based on the frequency with which they are inherited together versus independently. The closer two polymorphisms are together in a chromosome the higher the probability that they are inherited together. Integration of the relative positions of all the polymorphisms and associated marker SDFs can produce a genetic map of the species, where the distances between markers reflect the recombination frequencies in that chromosome segment.

The use of recombinant inbred lines for such genetic mapping is described for *Arabidopsis* by Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.) and for corn by Burr ("Mapping Genes with Recombinant Inbreds", pp. 249-254. In Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; Gardiner, J. et al., (1993) *Genetics* 134: 917). This procedure, however, is not limited to plants and can be used for other organisms (such as yeast) or for individual cells.

The SDFs of the present invention can also be used for simple sequence repeat (SSR) mapping. Rice SSR mapping is described by Morgante et al. (*The Plant Journal* (1993) 3: 165), Panaud et al. (*Genome* (1995) 38: 1170); Senior et al. (*Crop Science* (1996) 36: 1676), Taramino et al. (*Genome* (1996) 39: 277) and Ahn et al. (*Molecular and General Genetics* (1993) 241: 483-90). SSR mapping can be achieved using various methods. In one instance, polymorphisms are identified when sequence specific probes contained within an SDF flanking an SSR are made and used in polymerase chain reaction (PCR) assays with template DNA from two or more individuals of interest. Here, a change in the number of tandem repeats between the SSR-flanking sequences produces differently sized fragments (U.S. Pat. No. 5,766,847). Alternatively, polymorphisms can be identified by using the PCR fragment produced from the SSR-flanking sequence specific primer reaction as a probe against Southern blots representing different individuals (U. H. Refseth et al., (1997) *Electrophoresis* 18: 1519).

Genetic and physical maps of crop species have many uses. For example, these maps can be used to devise positional cloning strategies for isolating novel genes from the mapped crop species. In addition, because the genomes of closely related species are largely syntenic (that is, they display the same ordering of genes within the genome), these maps can be used to isolate novel alleles from relatives of crop species by positional cloning strategies.

The various types of maps discussed above can be used with the SDFs of the invention to identify Quantitative Trait Loci (QTLs). Many important crop traits, such as the solids content of tomatoes, are quantitative traits and result from the combined interactions of several genes. These genes reside at different loci in the genome, oftentimes on different chromosomes, and generally exhibit multiple alleles at each locus. The SDFs of the invention can be used to identify QTLs and isolate specific alleles as described by de Vicente and Tanksley (*Genetics* 134:585 (1993)). In addition to isolating QTL alleles in present crop species, the SDFs of the invention can also be used to isolate alleles from the corresponding QTL of wild relatives. Transgenic plants having various combinations of QTL alleles can then be created and the effects of the combinations measured. Once a desired allele combination has been identified, crop improvement can be accomplished either through biotechnological means or by directed conventional breeding programs (for review see Tanksley and McCouch, *Science* 277:1063 (1997)).

In another embodiment, the SDFs can be used to help create physical maps of the genome of corn, *Arabidopsis* and related species. Where SDFs have been ordered on a genetic map, as described above, they can be used as probes to discover which clones in large libraries of plant DNA fragments in YACs, BACs, etc. contain the same SDF or similar sequences, thereby facilitating the assignment of the large DNA fragments to chromosomal positions. Subsequently, the large BACs, YACs, etc. can be ordered unambiguously by more detailed studies of their sequence composition (e.g. Marra et al. (1997) Genomic Research 7:1072-1084) and by using their end or other sequences to find the identical sequences in other cloned DNA fragments. The overlapping of DNA sequences in this way allows large contigs of plant sequences to be built that, when sufficiently extended, provide a complete physical map of a chromosome. Sometimes the SDFs themselves will provide the means of joining cloned sequences into a contig.

The patent publication WO95/35505 and U.S. Pat. Nos. 5,445,943 and 5,410,270 describe scanning multiple alleles of a plurality of loci using hybridization to arrays of oligonucleotides. These techniques are useful for each of the types of mapping discussed above.

Following the procedures described above and using a plurality of the SDFs of the present invention, any individual can be genotyped. These individual genotypes can be used for the identification of particular cultivars, varieties, lines, ecotypes and genetically modified plants or can serve as tools for subsequent genetic studies involving multiple phenotypic traits.

B.3 Southern Blot Hybridization

The sequences from the REF and SEQ Tables can be used as probes for various hybridization techniques. These techniques are useful for detecting target polynucleotides in a sample or for determining whether transgenic plants, seeds or host cells harbor a gene or sequence of interest and thus might be expected to exhibit a particular trait or phenotype.

In addition, the SDFs from the invention can be used to isolate additional members of gene families from the same or different species and/or orthologous genes from the same or different species. This is accomplished by hybridizing an SDF to, for example, a Southern blot containing the appropriate genomic DNA or cDNA. Given the resulting hybridization data, one of ordinary skill in the art could distinguish and isolate the correct DNA fragments by size, restriction sites, sequence and stated hybridization conditions from a gel or from a library.

Identification and isolation of orthologous genes from closely related species and alleles within a species is particularly desirable because of their potential for crop improvement. Many important crop traits, such as the solid content of tomatoes, result from the combined interactions of the products of several genes residing at different loci in the genome. Generally, alleles at each of these loci can make quantitative differences to the trait. By identifying and isolating numerous alleles for each locus from within or different species, transgenic plants with various combinations of alleles can be created and the effects of the combinations measured. Once a more favorable allele combination has been identified, crop improvement can be accomplished either through biotechnological means or by directed conventional breeding programs (Tanksley et al. *Science* 277: 1063 (1997)).

The results from hybridizations of the SDFs of the invention to, for example, Southern blots containing DNA from another species can also be used to generate restriction fragment maps for the corresponding genomic regions. These maps provide additional information about the relative positions of restriction sites within fragments, further distinguishing mapped DNA from the remainder of the genome.

Physical maps can be made by digesting genomic DNA with different combinations of restriction enzymes.

Probes for Southern blotting to distinguish individual restriction fragments can range in size from 15 to 20 nucleotides to several thousand nucleotides. More preferably, the probe is 100 to 1,000 nucleotides long for identifying members of a gene family when it is found that repetitive sequences would complicate the hybridization. For identifying an entire corresponding gene in another species, the probe is more preferably the length of the gene, typically 2,000 to 10,000 nucleotides, but probes 50-1,000 nucleotides long might be used. Some genes, however, might require probes up to 1,500 nucleotides long or overlapping probes constituting the full-length sequence to span their lengths.

Also, while it is preferred that the probe be homogeneous with respect to its sequence, it is not necessary. For example, as described below, a probe representing members of a gene family having diverse sequences can be generated using PCR to amplify genomic DNA or RNA templates using primers derived from SDFs that include sequences that define the gene family.

For identifying corresponding genes in another species, the next most preferable probe is a cDNA spanning the entire coding sequence, which allows all of the mRNA-coding fragment of the gene to be identified. Probes for Southern blotting can easily be generated from SDFs by making primers having the sequence at the ends of the SDF and using corn or *Arabidopsis* genomic DNA as a template. In instances where the SDF includes sequence conserved among species, primers including the conserved sequence can be used for PCR with genomic DNA from a species of interest to obtain a probe.

Similarly, if the SDF includes a domain of interest, that fragment of the SDF can be used to make primers and, with appropriate template DNA, used to make a probe to identify genes containing the domain. Alternatively, the PCR products can be resolved, for example by gel electrophoresis, and cloned and/or sequenced. Using Southern hybridization, the variants of the domain among members of a gene family, both within and across species, can be examined.

B.4.1 Isolating DNA from Related Organisms

The SDFs of the invention can be used to isolate the corresponding DNA from other organisms. Either cDNA or genomic DNA can be isolated. For isolating genomic DNA, a lambda, cosmid, BAC or YAC, or other large insert genomic library from the plant of interest can be constructed using standard molecular biology techniques as described in detail by Sambrook et al. 1989 (Molecular Cloning: A Laboratory Manual, $2^{nd}$ ed. Cold Spring Harbor Laboratory Press, New York) and by Ausubel et al. 1992 (Current Protocols in Molecular Biology, Greene Publishing, New York).

To screen a phage library, for example, recombinant lambda clones are plated out on appropriate bacterial medium using an appropriate *E. coli* host strain. The resulting plaques are lifted from the plates using nylon or nitrocellulose filters. The plaque lifts are processed through denaturation, neutralization, and washing treatments following the standard protocols outlined by Ausubel et al. (1992). The plaque lifts are hybridized to either radioactively labeled or non-radioactively labeled SDF DNA at room temperature for about 16 hours, usually in the presence of 50% formamide and 5×SSC (sodium chloride and sodium citrate) buffer and blocking reagents. The plaque lifts are then washed at 42° C. with 1% Sodium Dodecyl Sulfate (SDS) and at a particular concentration of SSC. The SSC concentration used is dependent upon the stringency at which hybridization occurred in the initial Southern blot analysis performed. For example, if a fragment hybridized under medium stringency (e.g., Tm−20° C.), then this condition is maintained or preferably adjusted to a less stringent condition (e.g., Tm−30° C.) to wash the plaque lifts. Positive clones show detectable hybridization e.g., by exposure to X-ray films or chromogen formation. The positive clones are then subsequently isolated for purification using the same general protocol outlined above. Once the clone is purified, restriction analysis can be conducted to narrow the region corresponding to the gene of interest. The restriction analysis and succeeding subcloning steps can be done using procedures described by, for example Sambrook et al. (1989) cited above.

The procedures outlined for the lambda library are essentially similar to those used for YAC library screening, except that the YAC clones are harbored in bacterial colonies. The YAC clones are plated out at reasonable density on nitrocellulose or nylon filters supported by appropriate bacterial medium in petri plates. Following the growth of the bacterial clones, the filters are processed through the denaturation, neutralization, and washing steps following the procedures of Ausubel et al. 1992. The same hybridization procedures for lambda library screening are followed.

To isolate cDNA, similar procedures using appropriately modified vectors are employed. For instance, the library can be constructed in a lambda vector appropriate for cloning cDNA such as λgt11. Alternatively, the cDNA library can be made in a plasmid vector. cDNA for cloning can be prepared by any of the methods known in the art, but is preferably prepared as described above. Preferably, a cDNA library will include a high proportion of full-length clones.

B. 5. Isolating and/or Identifying Orthologous Genes

Probes and primers of the invention can be used to identify and/or isolate polynucleotides related to those in the REF and SEQ Tables. Related polynucleotides are those that are native to other plant organisms and exhibit either similar sequence or encode polypeptides with similar biological activity. One specific example is an orthologous gene. Orthologous genes have the same functional activity. As such, orthologous genes may be distinguished from homologous genes. The percentage of identity is a function of evolutionary separation and, in closely related species, the percentage of identity can be 98 to 100%. The amino acid sequence of a protein encoded by an orthologous gene can be less than 75% identical, but tends to be at least 75% or at least 80% identical, more preferably at least 90%, most preferably at least 95% identical to the amino acid sequence of the reference protein.

To find orthologous genes, the probes are hybridized to nucleic acids from a species of interest under low stringency conditions, preferably one where sequences containing as much as 40-45% mismatches will be able to hybridize. This condition is established by $T_m$–40° C. to Tm–48° C. (see below). Blots are then washed under conditions of increasing stringency. It is preferable that the wash stringency be such that sequences that are 85 to 100% identical will hybridize. More preferably, sequences 90 to 100% identical will hybridize and most preferably only sequences greater than 95% identical will hybridize. One of ordinary skill in the art will recognize that, due to degeneracy in the genetic code, amino acid sequences that are identical can be encoded by DNA sequences as little as 67% identical or less. Thus, it is preferable, for example, to make an overlapping series of shorter probes, on the order of 24 to 45 nucleotides, and individually hybridize them to the same arrayed library to avoid the problem of degeneracy introducing large numbers of mismatches.

As evolutionary divergence increases, genome sequences also tend to diverge. Thus, one of skill will recognize that searches for orthologous genes between more divergent species will require the use of lower stringency conditions compared to searches between closely related species. Also, degeneracy of the genetic code is more of a problem for searches in the genome of a species more distant evolutionarily from the species that is the source of the SDF probe sequences.

Therefore the method described in Bouckaert et al., U.S. Ser. No. 60/121,700, filed Feb. 25, 1999, hereby incorporated in its entirety by reference, can be applied to the SDFs of the present invention to isolate related genes from plant species which do not hybridize to the corn Arabidopsis, soybean, rice, wheat, and other plant sequences of the REF and SEQ Tables.

Identification of the relationship of nucleotide or amino acid sequences among plant species can be done by comparing the nucleotide or amino acid sequences of SDFs of the present application with nucleotide or amino acid sequences of other SDFs.

The SDFs of the invention can also be used as probes to search for genes that are related to the SDF within a species. Such related genes are typically considered to be members of a gene family. In such a case, the sequence similarity will often be concentrated into one or a few fragments of the sequence. The fragments of similar sequence that define the gene family typically encode a fragment of a protein or RNA that has an enzymatic or structural function. The percentage of identity in the amino acid sequence of the domain that defines the gene family is preferably at least 70%, more preferably 80 to 95%, most preferably 85 to 99%. To search for members of a gene family within a species, a low stringency hybridization is usually performed, but this will depend upon the size, distribution and degree of sequence divergence of domains that define the gene family. SDFs encompassing regulatory regions can be used to identify coordinately expressed genes by using the regulatory region sequence of the SDF as a probe.

In the instances where the SDFs are identified as being expressed from genes that confer a particular phenotype, then the SDFs can also be used as probes to assay plants of different species for those phenotypes.

I.C. Methods to Inhibit Gene Expression

The nucleic acid molecules of the present invention can be used to inhibit gene transcription and/or translation. Example of such methods include, without limitation:

Antisense Constructs;
Ribozyme Constructs;
Chimeraplast Constructs;
Co-Suppression;
Transcriptional Silencing; and
Other Methods of Gene Expression.

C.1 Antisense

In some instances it is desirable to suppress expression of an endogenous or exogenous gene. A well-known instance is the FLAVOR-SAVOR™ tomato, in which the gene encoding ACC synthase is inactivated by an antisense approach, thus delaying softening of the fruit after ripening. See for example, U.S. Pat. No. 5,859,330; U.S. Pat. No. 5,723,766; Oeller, et al, Science, 254:437-439 (1991); and Hamilton et al, Nature, 346:284-287 (1990). Also, timing of flowering can be controlled by suppression of the FLOWERING LOCUS C (FLC); high levels of this transcript are associated with late flowering, while absence of FLC is associated with early flowering (S. D. Michaels et al., Plant Cell 11:949 (1999). Also, the transition of apical meristem from production of leaves with associated shoots to flowering is regulated by TERMINAL FLOWER1, APETALA1 and LEAFY. Thus, when it is desired to induce a transition from shoot production to flowering, it is desirable to suppress TFL1 expression (S. J. Liljegren, Plant Cell 11:1007 (1999)). As another instance, arrested ovule development and female sterility result from suppression of the ethylene forming enzyme but can be reversed by application of ethylene (D. De Martinis et al., Plant Cell 11:1061 (1999)). The ability to manipulate female fertility of plants is useful in increasing fruit production and creating hybrids.

In the case of polynucleotides used to inhibit expression of an endogenous gene, the introduced sequence need not be perfectly identical to a sequence of the target endogenous gene. The introduced polynucleotide sequence will typically be at least substantially identical to the target endogenous sequence.

Some polynucleotide SDFs in the REF and SEQ Tables represent sequences that are expressed in corn, wheat, rice, soybean *Arabidopsis* and/or other plants. Thus the invention includes using these sequences to generate antisense constructs to inhibit translation and/or degradation of transcripts of said SDFs, typically in a plant cell.

To accomplish this, a polynucleotide segment from the desired gene that can hybridize to the mRNA expressed from the desired gene (the "antisense segment") is operably linked to a promoter such that the antisense strand of RNA will be transcribed when the construct is present in a host cell. A regulated promoter can be used in the construct to control transcription of the antisense segment so that transcription occurs only under desired circumstances.

The antisense segment to be introduced generally will be substantially identical to at least a fragment of the endogenous gene or genes to be repressed. The sequence, however, need not be perfectly identical to inhibit expression. Further, the antisense product may hybridize to the untranslated region instead of or in addition to the coding sequence of the gene. The vectors of the present invention can be designed such that the inhibitory effect applies to other proteins within a family of genes exhibiting homology or substantial homology to the target gene.

For antisense suppression, the introduced antisense segment sequence also need not be full length relative to either the primary transcription product or the fully processed mRNA. Generally, a higher percentage of sequence identity can be used to compensate for the use of a shorter sequence. Furthermore, the introduced sequence need not have the same intron or exon pattern, and homology of non-coding segments may be equally effective. Normally, a sequence of between about 30 or 40 nucleotides and the full length of the transcript can be used, though a sequence of at least about 100 nucleotides is preferred, a sequence of at least about 200 nucleotides is more preferred, and a sequence of at least about 500 nucleotides is especially preferred.

C.2. Ribozymes

It is also contemplated that gene constructs representing ribozymes and based on the SDFs in the REF and SEQ Tables are an object of the invention. Ribozymes can also be used to inhibit expression of genes by suppressing the translation of the mRNA into a polypeptide. It is possible to design ribozymes that specifically pair with virtually any target RNA and cleave the phosphodiester bacone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs, which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585 (1988).

Like the antisense constructs above, the ribozyme sequence fragment necessary for pairing need not be identical to the target nucleotides to be cleaved, nor identical to the sequences in the REF and SEQ Tables. Ribozymes may be constructed by combining the ribozyme sequence and some fragment of the target gene which would allow recognition of the target gene mRNA by the resulting ribozyme molecule. Generally, the sequence in the ribozyme capable of binding to the target sequence exhibits a percentage of sequence identity with at least 80%, preferably with at least 85%, more preferably with at least 90% and most preferably with at least 95%, even more preferably, with at least 96%, 97%, 98% or 99% sequence identity to some fragment of a sequence in the REF and SEQ Tables or the complement thereof. The ribozyme can be equally effective in inhibiting mRNA translation by cleaving either in the untranslated or coding regions. Generally, a higher percentage of sequence identity can be used to compensate for the use of a shorter sequence. Furthermore, the introduced sequence need not have the same intron or exon pattern, and homology of non-coding segments may be equally effective.

C.3. Chimeraplasts

The SDFs of the invention, such as those described by the REF and SEQ Tables, can also be used to construct chimeraplasts that can be introduced into a cell to produce at least one specific nucleotide change in a sequence corresponding to the SDF of the invention. A chimeraplast is an oligonucleotide comprising DNA and/or RNA that specifically hybridizes to a target region in a manner which creates a mismatched base-pair. This mismatched base-pair signals the cell's repair enzyme machinery which acts on the mismatched region resulting in the replacement, insertion or deletion of designated nucleotide(s). The altered sequence is then expressed by the cell's normal cellular mechanisms. Chimeraplasts can be designed to repair mutant genes, modify genes, introduce site-specific mutations, and/or act to interrupt or alter normal gene function (U.S. Pat. Nos. 6,010,907 and 6,004,804; and PCT Pub. No. WO99/58723 and WO99/07865).

C.4. Sense Suppression

The SDFs of the REF and SEQ Tables of the present invention are also useful to modulate gene expression by sense suppression. Sense suppression represents another method of gene suppression by introducing at least one exogenous copy or fragment of the endogenous sequence to be suppressed.

Introduction of expression cassettes in which a nucleic acid is configured in the sense orientation with respect to the promoter into the chromosome of a plant or by a self-replicating virus has been shown to be an effective means by which to induce degradation of mRNAs of target genes. For an example of the use of this method to modulate expression of endogenous genes see, Napoli et al., *The Plant Cell* 2:279 (1990), and U.S. Pat. Nos. 5,034,323, 5,231,020, and 5,283,184. Inhibition of expression may require some transcription of the introduced sequence.

For sense suppression, the introduced sequence generally will be substantially identical to the endogenous sequence intended to be inactivated. The minimal percentage of sequence identity will typically be greater than about 65%, but a higher percentage of sequence identity might exert a more effective reduction in the level of normal gene products. Sequence identity of more than about 80% is preferred, though about 95% to absolute identity would be most preferred. As with antisense regulation, the effect would likely apply to any other proteins within a similar family of genes exhibiting homology or substantial homology to the suppressing sequence.

C.5. Transcriptional Silencing

The nucleic acid sequences of the invention, including the SDFs of the REF and SEQ Tables, and fragments thereof, contain sequences that can be inserted into the genome of an organism resulting in transcriptional silencing. Such regulatory sequences need not be operatively linked to coding sequences to modulate transcription of a gene. Specifically, a promoter sequence without any other element of a gene can be introduced into a genome to transcriptionally silence an endogenous gene (see, for example, Vaucheret, H et al. (1998) The Plant Journal 16: 651-659). As another example, triple helices can be formed using oligonucleotides based on sequences from the REF and SEQ Tables, fragments thereof, and substantially similar sequence thereto. The oligonucleotide can be delivered to the host cell and can bind to the promoter in the genome to form a triple helix and prevent transcription. An oligonucleotide of interest is one that can bind to the promoter and block binding of a transcription factor to the promoter. In such a case, the oligonucleotide can be complementary to the sequences of the promoter that interact with transcription binding factors.

C.6. Other Methods to Inhibit Gene Expression

Yet another means of suppressing gene expression is to insert a polynucleotide into the gene of interest to disrupt transcription or translation of the gene.

Low frequency homologous recombination can be used to target a polynucleotide insert to a gene by flanking the polynucleotide insert with sequences that are substantially similar to the gene to be disrupted. Sequences from the REF and SEQ Tables, fragments thereof, and substantially similar sequence thereto can be used for homologous recombination.

In addition, random insertion of polynucleotides into a host cell genome can also be used to disrupt the gene of interest. Azpiroz-Leehan et al., *Trends in Genetics* 13:152 (1997). In this method, screening for clones from a library containing random insertions is preferred to identifying those that have polynucleotides inserted into the gene of interest. Such screening can be performed using probes and/or primers described above based on sequences from the REF and SEQ Tables, fragments thereof, and substantially similar sequence thereto. The screening can also be performed by selecting clones or $R_1$ plants having a desired phenotype.

I.D. Methods of Functional Analysis

The constructs described in the methods under I.C. above can be used to determine the function of the polypeptide encoded by the gene that is targeted by the constructs.

Down-regulating the transcription and translation of the targeted gene in the host cell or organisms, such as a plant, may produce phenotypic changes as compared to a wild-type cell or organism. In addition, in vitro assays can be used to determine if any biological activity, such as calcium flux, DNA transcription, nucleotide incorporation, etc., are being modulated by the down-regulation of the targeted gene.

Coordinated regulation of sets of genes, e.g., those contributing to a desired polygenic trait, is sometimes necessary to obtain a desired phenotype. SDFs of the invention representing transcription activation and DNA binding domains can be assembled into hybrid transcriptional activators. These hybrid transcriptional activators can be used with their corresponding DNA elements (i.e., those bound by the DNA-binding SDFs) to effect coordinated expression of desired genes (J. J. Schwarz et al., *Mol. Cell. Biol.* 12:266 (1992), A. Martinez et al., *Mol. Gen. Genet.* 261:546 (1999)).

The SDFs of the invention can also be used in the two-hybrid genetic systems to identify networks of protein-protein interactions (L. McAlister-Henn et al., *Methods* 19:330 (1999), J. C. Hu et al., *Methods* 20:80 (2000), M. Golovkin et al., *J. Biol. Chem.* 274:36428 (1999), K. Ichimura et al., *Biochem. Biophys. Res. Comm.* 253:532 (1998)). The SDFs of the invention can also be used in various expression display methods to identify important protein-DNA interactions (e.g. B. Luo et al., *J. Mol. Biol.* 266:479 (1997)).

I.E. Promoters

The SDFs of the invention are also useful as structural or regulatory sequences in a construct for modulating the expression of the corresponding gene in a plant or other organism, e.g. a symbiotic bacterium. For example, promoter sequences associated to SDFs of the REF and SEQ Tables of the present invention can be useful in directing expression of coding sequences either as constitutive promoters or to direct expression in particular cell types, tissues, or organs or in response to environmental stimuli.

With respect to the SDFs of the present invention a promoter is likely to be a relatively small portion of a genomic DNA (gDNA) sequence located in the first 2000 nucleotides upstream from an initial exon identified in a gDNA sequence or initial "ATG" or methionine codon or translational start site in a corresponding cDNA sequence. Such promoters are more likely to be found in the first 1000 nucleotides upstream of an initial ATG or methionine codon or translational start site of a cDNA sequence corresponding to a gDNA sequence. In particular, the promoter is usually located upstream of the transcription start site. The fragments of a particular gDNA sequence that function as elements of a promoter in a plant cell will preferably be found to hybridize to gDNA sequences presented and described in the REF and SEQ Tables at medium or high stringency, relevant to the length of the probe and its base composition.

Promoters are generally modular in nature. Promoters can consist of a basal promoter that functions as a site for assembly of a transcription complex comprising an RNA polymerase, for example RNA polymerase II. A typical transcription complex will include additional factors such as $TF_{II}B$, $TF_{II}D$, and $TF_{II}E$. Of these, $TF_{II}D$ appears to be the only one to bind DNA directly. The promoter might also contain one or more enhancers and/or suppressors that function as binding sites for additional transcription factors that have the function of modulating the level of transcription with respect to tissue specificity and of transcriptional responses to particular environmental or nutritional factors, and the like.

Short DNA sequences representing binding sites for proteins can be separated from each other by intervening sequences of varying length. For example, within a particular functional module, protein binding sites may be constituted by regions of 5 to 60, preferably 10 to 30, more preferably 10 to 20 nucleotides. Within such binding sites, there are typically 2 to 6 nucleotides that specifically contact amino acids of the nucleic acid binding protein. The protein binding sites are usually separated from each other by 10 to several hundred nucleotides, typically by 15 to 150 nucleotides, often by 20 to 50 nucleotides. DNA binding sites in promoter elements often display dyad symmetry in their sequence. Often elements binding several different proteins, and/or a plurality of sites that bind the same protein, will be combined in a region of 50 to 1,000 basepairs.

Elements that have transcription regulatory function can be isolated from their corresponding endogenous gene, or the desired sequence can be synthesized, and recombined in constructs to direct expression of a coding region of a gene in a desired tissue-specific, temporal-specific or other desired manner of inducibility or suppression. When hybridizations are performed to identify or isolate elements of a promoter by hybridization to the long sequences presented in the REF and SEQ Tables, conditions are adjusted to account for the above-described nature of promoters. For example short probes, constituting the element sought, are preferably used under low temperature and/or high salt conditions. When long probes, which might include several promoter elements are used, low to medium stringency conditions are preferred when hybridizing to promoters across species.

If a nucleotide sequence of an SDF, or part of the SDF, functions as a promoter or fragment of a promoter, then nucleotide substitutions, insertions or deletions that do not substantially affect the binding of relevant DNA binding proteins would be considered equivalent to the exemplified nucleotide sequence. It is envisioned that there are instances where it is desirable to decrease the binding of relevant DNA binding proteins to silence or down-regulate a promoter, or conversely to increase the binding of relevant DNA binding proteins to enhance or up-regulate a promoter and vice versa. In such instances, polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention. In addition, fragments of the promoter sequences described by the REF and SEQ Tables and variants thereof can be fused with other promoters or fragments to facilitate transcription and/or transcription in specific type of cells or under specific conditions.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

I.F. UTRs and Junctions

Polynucleotides comprising untranslated (UTR) sequences and intron/exon junctions are also within the scope of the invention. UTR sequences include introns and 5' or 3' untranslated regions (5' UTRs or 3' UTRs). Fragments of the sequences shown in the REF and SEQ Tables can comprise UTRs and intron/exon junctions.

These fragments of SDFs, especially UTRs, can have regulatory functions related to, for example, translation rate and mRNA stability. Thus, these fragments of SDFs can be isolated for use as elements of gene constructs for regulated production of polynucleotides encoding desired polypeptides.

Introns of genomic DNA segments might also have regulatory functions. Sometimes regulatory elements, especially transcription enhancer or suppressor elements, are found within introns. Also, elements related to stability of heteronuclear RNA and efficiency of splicing and of transport to the cytoplasm for translation can be found in intron elements. Thus, these segments can also find use as elements of expression vectors intended for use to transform plants.

Just as with promoters UTR sequences and intron/exon junctions can vary from those shown in the REF and SEQ Tables. Such changes from those sequences preferably will not affect the regulatory activity of the UTRs or intron/exon junction sequences on expression, transcription, or translation unless selected to do so. However, in some instances, down- or up-regulation of such activity may be desired to modulate traits or phenotypic or in vitro activity.

I.G. Coding Sequences

Isolated polynucleotides of the invention can include coding sequences that encode polypeptides comprising an amino acid sequence encoded by sequences in the REF and SEQ Tables or an amino acid sequence presented in the REF and SEQ Tables.

A nucleotide sequence encodes a polypeptide if a cell (or a cell free in vitro system) expressing that nucleotide sequence produces a polypeptide having the recited amino acid sequence when the nucleotide sequence is transcribed and the primary transcript is subsequently processed and translated by a host cell (or a cell free in vitro system) harboring the nucleic acid. Thus, an isolated nucleic acid that encodes a particular amino acid sequence can be a genomic sequence comprising exons and introns or a cDNA sequence that represents the product of splicing thereof. An isolated nucleic acid encoding an amino acid sequence also encompasses heteronuclear RNA, which contains sequences that are spliced out during expression, and mRNA, which lacks those sequences.

Coding sequences can be constructed using chemical synthesis techniques or by isolating coding sequences or by modifying such synthesized or isolated coding sequences as described above.

In addition to coding sequences encoding the polypeptide sequences of the REF and SEQ Tables, which are native to corn, *Arabidopsis*, soybean, rice, wheat, and other plants the isolated polynucleotides can be polynucleotides that encode variants, fragments, and fusions of those native proteins. Such polypeptides are described below in part II.

In variant polynucleotides generally, the number of substitutions, deletions or insertions is preferably less than 20%, more preferably less than 15%; even more preferably less than 10%, 5%, 3% or 1% of the number of nucleotides comprising a particularly exemplified sequence. It is generally expected that non-degenerate nucleotide sequence changes that result in 1 to 10, more preferably 1 to 5 and most preferably 1 to 3 amino acid insertions, deletions or substitutions will not greatly affect the function of an encoded polypeptide. The most preferred embodiments are those wherein 1 to 20, preferably 1 to 10, most preferably 1 to 5 nucleotides are added to, deleted from and/or substituted in the sequences specifically disclosed in the REF and SEQ Tables.

Insertions or deletions in polynucleotides intended to be used for encoding a polypeptide preferably preserve the reading frame. This consideration is not so important in instances when the polynucleotide is intended to be used as a hybridization probe.

II. Polypeptides and Proteins

IIA. Native Polypeptides and Proteins

Polypeptides within the scope of the invention include both native proteins as well as variants, fragments, and fusions thereof. Polypeptides of the invention are those encoded by any of the six reading frames of sequences shown in the REF and SEQ Tables, preferably encoded by the three frames reading in the 5' to 3' direction of the sequences as shown.

Native polypeptides include the proteins encoded by the sequences shown in the REF and SEQ Tables. Such native polypeptides include those encoded by allelic variants.

Polypeptide and protein variants will exhibit at least 75% sequence identity to those native polypeptides of the REF and SEQ Tables. More preferably, the polypeptide variants will exhibit at least 85% sequence identity; even more preferably, at least 90% sequence identity; more preferably at least 95%, 96%, 97%, 98%, or 99% sequence identity. Fragments of polypeptide or fragments of polypeptides will exhibit similar percentages of sequence identity to the relevant fragments of the native polypeptide. Fusions will exhibit a similar percentage of sequence identity in that fragment of the fusion represented by the variant of the native peptide.

Furthermore, polypeptide variants will exhibit at least one of the functional properties of the native protein. Such properties include, without limitation, protein interaction, DNA interaction, biological activity, immunological activity, receptor binding, signal transduction, transcription activity, growth factor activity, secondary structure, three-dimensional structure, etc. As to properties related to in vitro or in vivo activities, the variants preferably exhibit at least 60% of the activity of the native protein; more preferably at least 70%, even more preferably at least 80%, 85%, 90% or 95% of at least one activity of the native protein.

One type of variant of native polypeptides comprises amino acid substitutions, deletions and/or insertions. Conservative substitutions are preferred to maintain the function or activity of the polypeptide.

Within the scope of percentage of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide.

A.1 Antibodies

Isolated polypeptides can be utilized to produce antibodies. Polypeptides of the invention can generally be used, for example, as antigens for raising antibodies by known techniques. The resulting antibodies are useful as reagents for determining the distribution of the antigen protein within the tissues of a plant or within a cell of a plant. The antibodies are also useful for examining the production level of proteins in various tissues, for example in a wild-type plant or following genetic manipulation of a plant, by methods such as Western blotting.

Antibodies of the present invention, both polyclonal and monoclonal, may be prepared by conventional methods. In general, the polypeptides of the invention are first used to immunize a suitable animal, such as a mouse, rat, rabbit, or goat. Rabbits and goats are preferred for the preparation of polyclonal sera due to the volume of serum obtainable, and the availability of labeled anti-rabbit and anti-goat antibodies as detection reagents. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera is obtained by bleeding the immunized animal into a glass or plastic container, incubating the blood at 25° C. for one hour, followed by incubating the blood at 4° C. for 2-18 hours. The serum is recovered by centrifugation (e.g., 1,000×g for 10 minutes). About 20-50 ml per bleed may be obtained from rabbits.

Monoclonal antibodies are prepared using the method of Kohler and Milstein, Nature 256: 495 (1975), or modification thereof. Typically, a mouse or rat is immunized as described above. However, rather than bleeding the animal to extract serum, the spleen (and optionally several large lymph nodes) is removed and dissociated into single cells. If desired, the spleen cells can be screened (after removal of nonspecifically adherent cells) by applying a cell suspension to a plate, or well, coated with the protein antigen. B-cells producing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected Mab-secreting hybridomas are then cultured either in vitro (e.g., in tissue culture bottles or hollow fiber reactors), or in vivo (as ascites in mice).

Other methods for sustaining antibody-producing B-cell clones, such as by EBV transformation, are known.

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TNB) to a blue pigment, quantifiable with a spectrophotometer.

A.2 In Vitro Applications of Polypeptides

Some polypeptides of the invention will have enzymatic activities that are useful in vitro. For example, the soybean trypsin inhibitor (Kunitz) family is one of the numerous families of proteinase inhibitors. It comprises plant proteins which have inhibitory activity against serine proteinases from the trypsin and subtilisin families, thiol proteinases and aspartic proteinases. Thus, these peptides find in vitro use in protein purification protocols and perhaps in therapeutic settings requiring topical application of protease inhibitors.

Delta-aminolevulinic acid dehydratase (EC 4.2.1.24) (ALAD) catalyzes the second step in the biosynthesis of heme, the condensation of two molecules of 5-aminolevulinate to form porphobilinogen and is also involved in chlorophyll biosynthesis (Kaczor et al. (1994) Plant Physiol. 1-4: 1411-7; Smith (1988) Biochem. J. 249: 423-8; Schneider (1976) Z. naturforsch. [C] 31: 55-63). Thus, ALAD proteins can be used as catalysts in synthesis of heme derivatives. Enzymes of biosynthetic pathways generally can be used as catalysts for in vitro synthesis of the compounds representing products of the pathway.

Polypeptides encoded by SDFs of the invention can be engineered to provide purification reagents to identify and purify additional polypeptides that bind to them. This allows one to identify proteins that function as multimers or elucidate signal transduction or metabolic pathways. In the case of DNA binding proteins, the polypeptide can be used in a similar manner to identify the DNA determinants of specific binding (S. Pierrou et al., Anal. Biochem. 229:99 (1995), S. Chusacultanachai et al., J. Biol. Chem. 274:23591 (1999), Q. Lin et al., J. Biol. Chem. 272:27274 (1997)).

II.B. Polypeptide Variants, Fragments, and Fusions

Generally, variants, fragments, or fusions of the polypeptides encoded by the maximum length sequence (MLS) can exhibit at least one of the activities of the identified domains and/or related polypeptides described in Sections (C) and (D) of the REF Tables corresponding to the MLS of interest.

II.B.(1) Variants

A type of variant of the native polypeptides comprises amino acid substitutions. Conservative substitutions, described above (see II.), are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Within the scope of percentage of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide. Amino acid substitutions may also be made in the sequences; conservative substitutions being preferred.

One preferred class of variants are those that comprise (1) the domain of an encoded polypeptide and/or (2) residues conserved between the encoded polypeptide and related polypeptides. For this class of variants, the encoded polypeptide sequence is changed by insertion, deletion, or substitution at positions flanking the domain and/or conserved residues.

Another class of variants includes those that comprise an encoded polypeptide sequence that is changed in the domain or conserved residues by a conservative substitution.

Yet another class of variants includes those that lack one of the in vitro activities, or structural features of the encoded polypeptides. One example is polypeptides or proteins produced from genes comprising dominant negative mutations. Such a variant may comprise an encoded polypeptide sequence with non-conservative changes in a particular domain or group of conserved residues.

II.A.(2) Fragments

Fragments of particular interest are those that comprise a domain identified for a polypeptide encoded by an MLS of the instant invention and variants thereof. Also, fragments that comprise at least one region of residues conserved between an MLS encoded polypeptide and its related polypeptides are of great interest. Fragments are sometimes useful as polypeptides corresponding to genes comprising dominant negative mutations are.

II.A.(3) Fusions

Of interest are chimeras comprising (1) a fragment of the MLS encoded polypeptide or variants thereof of interest and (2) a fragment of a polypeptide comprising the same domain. For example, an AP2 helix encoded by a MLS of the invention fused to second AP2 helix from ANT protein, which comprises two AP2 helices. The present invention also encompasses fusions of MLS encoded polypeptides, variants, or fragments thereof fused with related proteins or fragments thereof.

Definition of Domains

The polypeptides of the invention may possess identifying domains as shown in the REF Tables. Specific domains within the MLS encoded polypeptides are indicated in the REF Tables. In addition, the domains within the MLS encoded polypeptide can be defined by the region that exhibits at least 70% sequence identity with the consensus sequences listed in the protein domain table of each of the domains.

The majority of the protein domain descriptions given in the protein domain table are obtained from Prosite and Pfam.

A. Activities of Polypeptides Comprising Signal Peptides

Polypeptides comprising signal peptides are a family of proteins that are typically targeted to (1) a particular organelle or intracellular compartment, (2) interact with a particular molecule or (3) for secretion outside of a host cell. Example of polypeptides comprising signal peptides include, without limitation, secreted proteins, soluble proteins, receptors, proteins retained in the ER, etc.

These proteins comprising signal peptides are useful to modulate ligand-receptor interactions, cell-to-cell communication, signal transduction, intracellular communication, and activities and/or chemical cascades that take part in an organism outside or within of any particular cell.

One class of such proteins are soluble proteins which are transported out of the cell. These proteins can act as ligands that bind to receptor to trigger signal transduction or to permit communication between cells.

Another class is receptor proteins which also comprise a retention domain that lodges the receptor protein in the membrane when the cell transports the receptor to the surface of the cell. Like the soluble ligands, receptors can also modulate signal transduction and communication between cells.

In addition the signal peptide itself can serve as a ligand for some receptors. An example is the interaction of the ER targeting signal peptide with the signal recognition particle (SRP). Here, the SRP binds to the signal peptide, halting translation, and the resulting SRP complex then binds to docking proteins located on the surface of the ER, prompting transfer of the protein into the ER.

A description of signal peptide residue composition is described below in Subsection IV.C.1.

III. Methods of Modulating Polypeptide Production

It is contemplated that polynucleotides of the invention can be incorporated into a host cell or in-vitro system to modulate polypeptide production. For instance, the SDFs prepared as described herein can be used to prepare expression cassettes useful in a number of techniques for suppressing or enhancing expression.

An example are polynucleotides comprising sequences to be transcribed, such as coding sequences, of the present invention can be inserted into nucleic acid constructs to modulate polypeptide production. Typically, such sequences to be transcribed are heterologous to at least one element of the nucleic acid construct to generate a chimeric gene or construct.

Another example of useful polynucleotides are nucleic acid molecules comprising regulatory sequences of the present invention. Chimeric genes or constructs can be generated when the regulatory sequences of the invention linked to heterologous sequences in a vector construct. Within the scope of invention are such chimeric gene and/or constructs.

Also within the scope of the invention are nucleic acid molecules, whereof at least a part or fragment of these DNA molecules are presented in the REF and SEQ Tables of the present application, and wherein the coding sequence is under the control of its own promoter and/or its own regulatory elements. Such molecules are useful for transforming the genome of a host cell or an organism regenerated from said host cell for modulating polypeptide production.

Additionally, a vector capable of producing the oligonucleotide can be inserted into the host cell to deliver the oligonucleotide.

More detailed description of components to be included in vector constructs are described both above and below.

Whether the chimeric vectors or native nucleic acids are utilized, such polynucleotides can be incorporated into a host cell to modulate polypeptide production. Native genes and/or nucleic acid molecules can be effective when exogenous to the host cell.

Methods of modulating polypeptide expression includes, without limitation:

Suppression methods, such as
Antisense
Ribozymes
Co-suppression
Insertion of Sequences into the Gene to be Modulated
Regulatory Sequence Modulation.
as well as Methods for Enhancing Production, such as
Insertion of Exogenous Sequences; and
Regulatory Sequence Modulation.

III.A. Suppression

Expression cassettes of the invention can be used to suppress expression of endogenous genes which comprise the SDF sequence. Inhibiting expression can be useful, for instance, to tailor the ripening characteristics of a fruit (Oeller et al., *Science* 254:437 (1991)) or to influence seed size (WO98/07842) or to provoke cell ablation (Mariani et al., Nature 357: 384-387 (1992).

As described above, a number of methods can be used to inhibit gene expression in plants, such as antisense, ribozyme, introduction of exogenous genes into a host cell, insertion of a polynucleotide sequence into the coding sequence and/or the promoter of the endogenous gene of interest, and the like.

III.A.1. Antisense

An expression cassette as described above can be transformed into host cell or plant to produce an antisense strand of RNA. For plant cells, antisense RNA inhibits gene expression by preventing the accumulation of mRNA which encodes the enzyme of interest, see, e.g., Sheehy et al., *Proc. Nat. Acad. Sci.* USA, 85:8805 (1988), and Hiatt et al., U.S. Pat. No. 4,801,340.

III.A.2. Ribozymes

Similarly, ribozyme constructs can be transformed into a plant to cleave mRNA and down-regulate translation.

III.A.3. Co-Suppression

Another method of suppression is by introducing an exogenous copy of the gene to be suppressed. Introduction of expression cassettes in which a nucleic acid is configured in the sense orientation with respect to the promoter has been shown to prevent the accumulation of mRNA. A detailed description of this method is described above.

III.A.4. Insertion of Sequences into the Gene to be Modulated

Yet another means of suppressing gene expression is to insert a polynucleotide into the gene of interest to disrupt transcription or translation of the gene.

Homologous recombination could be used to target a polynucleotide insert to a gene using the Cre-Lox system (A. C. Vergunst et al., *Nucleic Acids Res.* 26:2729 (1998), A. C. Vergunst et al., *Plant Mol. Biol.* 38:393 (1998), H. Albert et al., *Plant J.* 7:649 (1995)).

In addition, random insertion of polynucleotides into a host cell genome can also be used to disrupt the gene of interest. Azpiroz-Leehan et al., *Trends in Genetics* 13:152 (1997). In this method, screening for clones from a library containing random insertions is preferred for identifying those that have polynucleotides inserted into the gene of interest. Such screening can be performed using probes and/or primers described above based on sequences from the REF and SEQ Tables, fragments thereof, and substantially similar sequence thereto. The screening can also be performed by selecting clones or any transgenic plants having a desired phenotype.

III.A.5. Regulatory Sequence Modulation

The SDFs described in the REF and SEQ Tables, and fragments thereof are examples of nucleotides of the invention that contain regulatory sequences that can be used to suppress or inactivate transcription and/or translation from a gene of interest as discussed in I.C.5.

III.A.6. Genes Comprising Dominant-Negative Mutations

When suppression of production of the endogenous, native protein is desired it is often helpful to express a gene comprising a dominant negative mutation. Production of protein variants produced from genes comprising dominant negative mutations is a useful tool for research Genes comprising dominant negative mutations can produce a variant polypeptide which is capable of competing with the native polypeptide, but which does not produce the native result. Consequently, over expression of genes comprising these mutations can titrate out an undesired activity of the native protein. For example, The product from a gene comprising a dominant negative mutation of a receptor can be used to constitutively activate or suppress a signal transduction cascade, allowing examination of the phenotype and thus the trait(s) controlled by that receptor and pathway. Alternatively, the protein arising from the gene comprising a dominant-negative mutation can be an inactive enzyme still capable of binding to the same substrate as the native protein and therefore competes with such native protein.

Products from genes comprising dominant-negative mutations can also act upon the native protein itself to prevent activity. For example, the native protein may be active only as a homo-multimer or as one subunit of a hetero-multimer. Incorporation of an inactive subunit into the multimer with native subunit(s) can inhibit activity.

Thus, gene function can be modulated in host cells of interest by insertion into these cells vector constructs comprising a gene comprising a dominant-negative mutation.

III.B. Enhanced Expression

Enhanced expression of a gene of interest in a host cell can be accomplished by either (1) insertion of an exogenous gene; or (2) promoter modulation.

III.B.1. Insertion of an Exogenous Gene

Insertion of an expression construct encoding an exogenous gene can boost the number of gene copies expressed in a host cell.

Such expression constructs can comprise genes that either encode the native protein that is of interest or that encode a variant that exhibits enhanced activity as compared to the native protein. Such genes encoding proteins of interest can be constructed from the sequences from the REF and SEQ Tables, fragments thereof, and substantially similar sequence thereto.

Such an exogenous gene can include either a constitutive promoter permitting expression in any cell in a host organism or a promoter that directs transcription only in particular cells or times during a host cell life cycle or in response to environmental stimuli.

III.B.2. Regulatory Sequence Modulation

The SDFs of the REF and SEQ Tables, and fragments thereof, contain regulatory sequences that can be used to enhance expression of a gene of interest. For example, some of these sequences contain useful enhancer elements. In some cases, duplication of enhancer elements or insertion of exogenous enhancer elements will increase expression of a desired gene from a particular promoter. As other examples, all 11 promoters require binding of a regulatory protein to be activated, while some promoters may need a protein that signals a promoter binding protein to expose a polymerase binding site. In either case, over-production of such proteins can be used to enhance expression of a gene of interest by increasing the activation time of the promoter.

Such regulatory proteins are encoded by some of the sequences in the REF and SEQ Tables, fragments thereof, and substantially similar sequences thereto.

Coding sequences for these proteins can be constructed as described above.

IV. Gene Constructs and Vector Construction

To use isolated SDFs of the present invention or a combination of them or parts and/or mutants and/or fusions of said SDFs in the above techniques, recombinant DNA vectors which comprise said SDFs and are suitable for transformation of cells, such as plant cells, are usually prepared. The SDF construct can be made using standard recombinant DNA techniques (Sambrook et al. 1989) and can be introduced to the species of interest by *Agrobacterium*-mediated transformation or by other means of transformation (e.g., particle gun bombardment) as referenced below.

The vector bacone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);
(b) YAC: Burke et al., Science 236:806-812 (1987);
(c) PAC: Sternberg N. et al., Proc Natl Acad Sci USA. January; 87(1):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol Biol 170: 827-842 (1983); or Insertion vector, e.g., Huynh et al., In: Glover N M (ed) DNA Cloning: A practical Approach, Vol. 1 Oxford: IRL Press (1985);
(f) T-DNA gene fusion vectors: Walden et al., Mol Cell Biol 1: 175-194 (1990); and
(g) Plasmid vectors: Sambrook et al., infra.

Typically, a vector will comprise the exogenous gene, which in its turn comprises an SDF of the present invention to be introduced into the genome of a host cell, and which gene may be an antisense construct, a ribozyme construct chimeraplast, or a coding sequence with any desired transcriptional and/or translational regulatory sequences, such as promoters, UTRs, and 3' end termination sequences. Vectors of the invention can also include origins of replication, scaffold attachment regions (SARs), markers, homologous sequences, introns, etc.

A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for over-expression, a plant promoter fragment may be employed that will direct transcription of the gene in all tissues of a regenerated plant. Alternatively, the plant promoter may direct transcription of an SDF of the invention in a specific tissue (tissue-specific promoters) or may be otherwise under more precise environmental control (inducible promoters).

If proper polypeptide production is desired, a polyadenylation region at the 3'-end of the coding region is typically included. The polyadenylation region can be derived from the natural gene, from a variety of other plant genes, or from T-DNA.

The vector comprising the sequences from genes or SDF or the invention may comprise a marker gene that confers a selectable phenotype on plant cells. The vector can include promoter and coding sequence, for instance. For example, the marker may encode biocide resistance, particularly antibiotic resistance, such as resistance to kanamycin, G418, bleomycin, hygromycin, or herbicide resistance, such as resistance to chlorosulfuron or phosphinotricin.

IV.A. Coding Sequences

Generally, the sequence in the transformation vector and to be introduced into the genome of the host cell does not need to be absolutely identical to an SDF of the present invention. Also, it is not necessary for it to be full length, relative to either the primary transcription product or fully processed mRNA. Furthermore, the introduced sequence need not have the same intron or exon pattern as a native gene. Also, heterologous non-coding segments can be incorporated into the coding sequence without changing the desired amino acid sequence of the polypeptide to be produced.

IV.B. Promoters

As explained above, introducing an exogenous SDF from the same species or an orthologous SDF from another species can modulate the expression of a native gene corresponding to that SDF of interest. Such an SDF construct can be under the control of either a constitutive promoter or a highly regulated inducible promoter (e.g., a copper inducible promoter). The promoter of interest can initially be either endogenous or heterologous to the species in question. When re-introduced into the genome of said species, such promoter becomes exogenous to said species. Over-expression of an SDF transgene can lead to co-suppression of the homologous endogeneous sequence thereby creating some alterations in the phenotypes of the transformed species as demonstrated by similar analysis of the chalcone synthase gene (Napoli et al., *Plant Cell* 2:279 (1990) and van der Krol et al., *Plant Cell* 2:291 (1990)). If an SDF is found to encode a protein with desirable characteristics, its over-production can be controlled so that its accumulation can be manipulated in an organ- or tissue-specific manner utilizing a promoter having such specificity.

Likewise, if the promoter of an SDF (or an SDF that includes a promoter) is found to be tissue-specific or developmentally regulated, such a promoter can be utilized to drive or facilitate the transcription of a specific gene of interest (e.g., seed storage protein or root-specific protein).

Thus, the level of accumulation of a particular protein can be manipulated or its spatial localization in an organ- or tissue-specific manner can be altered.

IV.C Signal Peptides

SDFs of the present invention containing signal peptides are indicated in the REF and SEQ Tables. In some cases it may be desirable for the protein encoded by an introduced exogenous or orthologous SDF to be targeted (1) to a particular organelle intracellular compartment, (2) to interact with a particular molecule such as a membrane molecule or (3) for secretion outside of the cell harboring the introduced SDF. This will be accomplished using a signal peptide.

Signal peptides direct protein targeting, are involved in ligand-receptor interactions and act in cell to cell communication. Many proteins, especially soluble proteins, contain a signal peptide that targets the protein to one of several different intracellular compartments. In plants, these compartments include, but are not limited to, the endoplasmic reticulum (ER), mitochondria, plastids (such as chloroplasts), the vacuole, the Golgi apparatus, protein storage vessicles (PSV) and, in general, membranes. Some signal peptide sequences are conserved, such as the Asn-Pro-Ile-Arg amino acid motif found in the N-terminal propeptide signal that targets proteins to the vacuole (Marty (1999) *The Plant Cell* 11: 587-599). Other signal peptides do not have a consensus sequence per se, but are largely composed of hydrophobic amino acids, such as those signal peptides targeting proteins to the ER (Vitale and Denecke (1999) *The Plant Cell* 11: 615-628). Still others do not appear to contain either a consensus sequence or an identified common secondary sequence, for instance the chloroplast stromal targeting signal peptides (Keegstra and Cline (1999) *The Plant Cell* 11: 557-570). Furthermore, some targeting peptides are bipartite, directing proteins first to an organelle and then to a membrane within the organelle (e.g. within the thylakoid lumen of the chloroplast; see Keegstra and Cline (1999) *The Plant Cell* 11: 557-570). In addition to the diversity in sequence and secondary structure, placement of the signal peptide is also varied. Proteins destined for the vacuole, for example, have targeting signal peptides found at the N-terminus, at the C-terminus and at a surface location in mature, folded proteins. Signal peptides also serve as ligands for some receptors.

These characteristics of signal proteins can be used to more tightly control the phenotypic expression of introduced SDFs. In particular, associating the appropriate signal sequence with a specific SDF can allow sequestering of the protein in specific organelles (plastids, as an example), secretion outside of the cell, targeting interaction with particular receptors, etc. Hence, the inclusion of signal proteins in constructs involving the SDFs of the invention increases the range of manipulation of SDF phenotypic expression. The nucleotide sequence of the signal peptide can be isolated from characterized genes using common molecular biological techniques or can be synthesized in vitro.

In addition, the native signal peptide sequences, both amino acid and nucleotide, described in the REF and SEQ Tables can be used to modulate polypeptide transport. Further variants of the native signal peptides described in the REF and SEQ Tables are contemplated. Insertions, deletions, or substitutions can be made. Such variants will retain at least one of the functions of the native signal peptide as well as exhibiting some degree of sequence identity to the native sequence.

Also, fragments of the signal peptides of the invention are useful and can be fused with other signal peptides of interest to modulate transport of a polypeptide.

V. Transformation Techniques

A wide range of techniques for inserting exogenous polynucleotides are known for a number of host cells, including, without limitation, bacterial, yeast, mammalian, insect and plant cells.

Techniques for transforming a wide variety of higher plant species are well known and described in the technical and scientific literature. See, e.g. Weising et al., *Ann. Rev. Genet.* 22:421 (1988); and Christou, Euphytica, v. 85, n. 1-3:13-27, (1995).

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (McCormac et al., *Mol. Biotechnol.* 8:199 (1997); Hamilton, *Gene* 200:107 (1997)); Salomon et al. *EMBO J.* 3:141 (1984); Herrera-Estrella et al. *EMBO J.* 2:987 (1983).

Microinjection techniques are known in the art and well described in the scientific and patent literature. The introduction of DNA constructs using polyethylene glycol precipitation is described in Paszkowski et al. *EMBO J.* 3:2717 (1984). Electroporation techniques are described in Fromm et al. *Proc. Natl Acad. Sci. USA* 82:5824 (1985). Ballistic transformation techniques are described in Klein et al. *Nature* 327:773 (1987). *Agrobacterium tumefaciens*-mediated transformation techniques, including disarming and use of binary or co-integrate vectors, are well described in the scientific literature. See, for example Hamilton, C M., *Gene* 200:107 (1997); Müller et al. *Mol. Gen. Genet.* 207:171 (1987); Komari et al. *Plant J.* 10:165 (1996); Venkateswarlu et al. *Biotechnology* 9:1103 (1991) and Gleave, A P., *Plant Mol. Biol.* 20:1203 (1992); Graves and Goldman, *Plant Mol. Biol.* 7:34 (1986) and Gould et al., *Plant Physiology* 95:426 (1991).

Transformed plant cells which are derived by any of the above transformation techniques can be cultured to regenerate a whole plant that possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture* in "Handbook of Plant Cell Culture," pp. 124-176, MacMillan Publishing Company, New York, 1983; and Binding, *Regeneration of Plants, Plant Protoplasts*, pp. 21-73, CRC Press, Boca Raton, 1988. Regeneration can also be obtained from plant callus, explants, organs, or parts thereof. Such regeneration techniques are described generally in Klee et al. *Ann. Rev. of Plant Phys.* 38:467 (1987). Regeneration of monocots (rice) is described by Hosoyama et al. (*Biosci. Biotechnol. Biochem.* 58:1500 (1994)) and by Ghosh et al. (*J.*

Biotechnol. 32:1 (1994)). The nucleic acids of the invention can be used to confer desired traits on essentially any plant.

Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and, *Zea.*

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The particular sequences of SDFs identified are provided in the attached the REF and SEQ Tables. One of ordinary skill in the art, having this data, can obtain cloned DNA fragments, synthetic DNA fragments or polypeptides constituting desired sequences by recombinant methodology known in the art or described herein.

EXAMPLES

The invention is illustrated by way of the following examples. The invention is not limited by these examples as the scope of the invention is defined solely by the claims following.

Example 1: cDNA Preparation

A number of the nucleotide sequences disclosed in the REF and SEQ Tables herein as representative of the SDFs of the invention can be obtained by sequencing genomic DNA (gDNA) and/or cDNA from corn plants grown from HYBRID SEED #35A19, purchased from Pioneer Hi-Bred International, Inc., Supply Management, P.O. Box 256, Johnston, Iowa 50131-0256.

A number of the nucleotide sequences disclosed in the REF and SEQ Tables herein as representative of the SDFs of the invention can also be obtained by sequencing genomic DNA from *Arabidopsis thaliana*, Wassilewskija ecotype or by sequencing cDNA obtained from mRNA from such plants as described below. This is a true breeding strain. Seeds of the plant are available from the *Arabidopsis* Biological Resource Center at the Ohio State University, under the accession number CS2360. Seeds of this plant were deposited under the terms and conditions of the Budapest Treaty at the American Type Culture Collection, Manassas, Va. on Aug. 31, 1999, and were assigned ATCC No. PTA-595.

Other methods for cloning full-length cDNA are described, for example, by Seki et al., *Plant Journal* 15:707-720 (1998) "High-efficiency cloning of *Arabidopsis* full-length cDNA by biotinylated Cap trapper"; Maruyama et al., *Gene* 138:171 (1994) "Oligo-capping a simple method to replace the cap structure of eukaryotic mRNAs with oligoribonucleotides"; and WO 96/34981.

Tissues are, or each organ is, individually pulverized and frozen in liquid nitrogen. Next, the samples are homogenized in the presence of detergents and then centrifuged. The debris and nuclei are removed from the sample and more detergents are added to the sample. The sample is centrifuged and the debris is removed. Then the sample is applied to a 2M sucrose cushion to isolate polysomes. The RNA is isolated by treatment with detergents and proteinase K followed by ethanol precipitation and centrifugation. The polysomal RNA from the different tissues is pooled according to the following mass ratios: 15/15/1 for male inflorescences, female inflorescences and root, respectively. The pooled material is then used for cDNA synthesis by the methods described below.

Starting material for cDNA synthesis for the exemplary corn cDNA clones with sequences presented in the REF and SEQ Tables is poly(A)-containing polysomal mRNAs from inflorescences and root tissues of corn plants grown from HYBRID SEED #35A19. Male inflorescences and female (pre- and post-fertilization) inflorescences are isolated at various stages of development. Selection for poly(A) containing polysomal RNA is done using oligo d(T) cellulose columns, as described by Cox and Goldberg, "Plant Molecular Biology: A Practical Approach", pp. 1-35, Shaw ed., c. 1988 by IRL, Oxford. The quality and the integrity of the polyA+ RNAs are evaluated.

Starting material for cDNA synthesis for the exemplary *Arabidopsis* cDNA clones with sequences presented in the REF and SEQ Tables is polysomal RNA isolated from the top-most inflorescence tissues of *Arabidopsis thaliana* Wassilewskija (Ws.) and from roots of *Arabidopsis thaliana* Landsberg erecta (L. er.), also obtained from the *Arabidopsis* Biological Resource Center. Nine parts inflorescence to every part root is used, as measured by wet mass. Tissue is pulverized and exposed to liquid nitrogen. Next, the sample is homogenized in the presence of detergents and then centrifuged. The debris and nuclei are removed from the sample and more detergents are added to the sample. The sample is centrifuged and the debris is removed and the sample is applied to a 2M sucrose cushion to isolate polysomal RNA. Cox et al., "Plant Molecular Biology: A Practical Approach", pp. 1-35, Shaw ed., c. 1988 by IRL, Oxford. The polysomal RNA is used for cDNA synthesis by the methods described below. Polysomal mRNA is then isolated as described above for corn cDNA. The quality of the RNA is assessed electrophoretically.

Following preparation of the mRNAs from various tissues as described above, selection of mRNA with intact 5' ends and specific attachment of an oligonucleotide tag to the 5' end of such mRNA is performed using either a chemical or enzymatic approach. Both techniques take advantage of the presence of the "cap" structure, which characterizes the 5' end of most intact mRNAs and which comprises a guanosine generally methylated once, at the 7 position.

The chemical modification approach involves the optional elimination of the 2', 3'-cis diol of the 3' terminal ribose, the oxidation of the 2', 3'-cis diol of the ribose linked to the cap of the 5' ends of the mRNAs into a dialdehyde, and the coupling of the such obtained dialdehyde to a derivatized oligonucleotide tag. Further detail regarding the chemical approaches for obtaining mRNAs having intact 5' ends are disclosed in International Application No. WO96/34981 published Nov. 7, 1996.

The enzymatic approach for ligating the oligonucleotide tag to the intact 5' ends of mRNAs involves the removal of the phosphate groups present on the 5' ends of uncapped incomplete mRNAs, the subsequent decapping of mRNAs having intact 5' ends and the ligation of the phosphate present at the 5' end of the decapped mRNA to an oligonucleotide tag. Further detail regarding the enzymatic approaches for obtaining mRNAs having intact 5' ends are disclosed in Dumas Milne Edwards J. B. (Doctoral Thesis of Paris VI University, Le clonage des ADNc complets: difficultés et perspectives nouvelles. Apports pour l'étude de la régulation de l'expression de la tryptophane hydroxylase de rat, 20 Dec. 1993), EPO 625572 and Kato et al., *Gene* 150:243-250 (1994).

In both the chemical and the enzymatic approach, the oligonucleotide tag has a restriction enzyme site (e.g. an EcoRI site) therein to facilitate later cloning procedures. Following attachment of the oligonucleotide tag to the mRNA, the integrity of the mRNA is examined by performing a Northern blot using a probe complementary to the oligonucleotide tag.

For the mRNAs joined to oligonucleotide tags using either the chemical or the enzymatic method, first strand cDNA synthesis is performed using an oligo-dT primer with reverse transcriptase. This oligo-dT primer can contain an internal tag of at least 4 nucleotides, which can be different from one mRNA preparation to another. Methylated dCTP is used for cDNA first strand synthesis to protect the internal EcoRI sites from digestion during subsequent steps. The first strand cDNA is precipitated using isopropanol after removal of RNA by alkaline hydrolysis to eliminate residual primers.

Second strand cDNA synthesis is conducted using a DNA polymerase, such as Klenow fragment and a primer corresponding to the 5' end of the ligated oligonucleotide. The primer is typically 20-25 bases in length. Methylated dCTP is used for second strand synthesis in order to protect internal EcoRI sites in the cDNA from digestion during the cloning process.

Following second strand synthesis, the full-length cDNAs are cloned into a phagemid vector, such as pBlueScript™ (Stratagene). The ends of the full-length cDNAs are blunted with T4 DNA polymerase (Biolabs) and the cDNA is digested with EcoRI. Since methylated dCTP is used during cDNA synthesis, the EcoRI site present in the tag is the only hemi-methylated site; hence the only site susceptible to EcoRI digestion. In some instances, to facilitate subcloning, an Hind III adapter is added to the 3' end of full-length cDNAs.

The full-length cDNAs are then size fractionated using either exclusion chromatography (AcA, Biosepra) or electrophoretic separation which yields 3 to 6 different fractions. The full-length cDNAs are then directionally cloned either into pBlueScript™ using either the EcoRI and SmaI restriction sites or, when the Hind III adapter is present in the full-length cDNAs, the EcoRI and Hind III restriction sites. The ligation mixture is transformed, preferably by electroporation, into bacteria, which are then propagated under appropriate antibiotic selection.

Clones containing the oligonucleotide tag attached to full-length cDNAs are selected as follows.

The plasmid cDNA libraries made as described above are purified (e.g. by a column available from Qiagen). A positive selection of the tagged clones is performed as follows. Briefly, in this selection procedure, the plasmid DNA is converted to single stranded DNA using phage F1 gene II endonuclease in combination with an exonuclease (Chang et al., *Gene* 127:95 (1993)) such as exonuclease III or T7 gene 6 exonuclease. The resulting single stranded DNA is then purified using paramagnetic beads as described by Fry et al., *Biotechniques* 13: 124 (1992). Here the single stranded DNA is hybridized with a biotinylated oligonucleotide having a sequence corresponding to the 3' end of the oligonucleotide tag. Preferably, the primer has a length of 20-25 bases. Clones including a sequence complementary to the biotinylated oligonucleotide are selected by incubation with streptavidin coated magnetic beads followed by magnetic capture. After capture of the positive clones, the plasmid DNA is released from the magnetic beads and converted into double stranded DNA using a DNA polymerase such as ThermoSequenase™ (obtained from Amersham Pharmacia Biotech). Alternatively, protocols such as the Gene Trapper™ kit (Gibco BRL) can be used. The double stranded DNA is then transformed, preferably by electroporation, into bacteria. The percentage of positive clones having the 5' tag oligonucleotide is typically estimated to be between 90 and 98% from dot blot analysis.

Following transformation, the libraries are ordered in microtiter plates and sequenced. The *Arabidopsis* library was deposited at the American Type Culture Collection on Jan. 7, 2000 as "*E-coli* liba 010600" under the accession number PTA-1161.

Example 2: Southern Hybridizations

The SDFs of the invention can be used in Southern hybridizations as described above. The following describes extraction of DNA from nuclei of plant cells, digestion of the nuclear DNA and separation by length, transfer of the separated fragments to membranes, preparation of probes for hybridization, hybridization and detection of the hybridized probe.

The procedures described herein can be used to isolate related polynucleotides or for diagnostic purposes. Moderate stringency hybridization conditions, as defined above, are described in the present example. These conditions result in detection of hybridization between sequences having at least 70% sequence identity. As described above, the hybridization and wash conditions can be changed to reflect the desired percentage of sequence identity between probe and target sequences that can be detected.

In the following procedure, a probe for hybridization is produced from two PCR reactions using two primers from genomic sequence of *Arabidopsis thaliana*. As described above, the particular template for generating the probe can be any desired template.

The first PCR product is assessed to validate the size of the primer to assure it is of the expected size. Then the product of the first PCR is used as a template, with the same pair of primers used in the first PCR, in a second PCR that produces a labeled product used as the probe.

Fragments detected by hybridization, or other bands of interest, can be isolated from gels used to separate genomic DNA fragments by known methods for further purification and/or characterization.

Buffers for Nuclear DNA Extraction
1. 10×HB

| | 1000 ml | |
|---|---|---|
| 40 mM spermidine | 10.2 g | Spermine (Sigma S-2876) and spermidine (Sigma S-2501) |
| 10 mM spermine | 3.5 g | Stabilize chromatin and the nuclear membrane |
| 0.1M EDTA (disodium) | 37.2 g | EDTA inhibits nuclease |
| 0.1M Tris | 12.1 g | Buffer |
| 0.8M KCl | 59.6 g | Adjusts ionic strength for stability of nuclei |

Adjust pH to 9.5 with 10 N NaOH. It appears that there is a nuclease present in leaves. Use of pH 9.5 appears to inactivate this nuclease.

2. 2 M sucrose (684 g per 1000 ml)
   Heat about half the final volume of water to about 50° C. Add the sucrose slowly then bring the mixture to close to final volume; stir constantly until it has dissolved. Bring the solution to volume.
3. Sarkosyl solution (lyses nuclear membranes)

|  | 1000 ml |
| --- | --- |
| N-lauroyl sarcosine (Sarkosyl) | 20.0 g |
| 0.1M Tris | 12.1 g |
| 0.04M EDTA (Disodium) | 14.9 g |

Adjust the pH to 9.5 after all the components are dissolved and bring up to the proper volume.
4. 20% Triton X-100
   80 ml Triton X-100
   320 ml 1×HB (w/o β-ME and PMSF)
   Prepare in advance; Triton takes some time to dissolve
A. Procedure
1. Prepare 1× "H" buffer (keep ice-cold during use)

|  | 1000 ml |  |
| --- | --- | --- |
| 10X HB | 100 ml |  |
| 2M sucrose | 250 ml | a non-ionic osmoticum |
| Water | 634 ml |  |

Added Just Before Use:

| 100 mM PMSF* | 10 ml | a protease inhibitor; protects nuclear membrane proteins |
| --- | --- | --- |
| β-mercaptoethanol | 1 ml | inactivates nuclease by reducing disulfide bonds |

*100 mM PMSF
(phenyl methyl sulfonyl fluoride, Sigma P-7626)
(add 0.0875 g to 5 ml 100% ethanol)

2. Homogenize the tissue in a blender (use 300-400 ml of 1×HB per blender). Be sure that you use 5-10 ml of HB buffer per gram of tissue. Blenders generate heat so be sure to keep the homogenate cold. It is necessary to put the blenders in ice periodically.
3. Add the 20% Triton X-100 (25 ml per liter of homogenate) and gently stir on ice for 20 min. This lyses plastid, but not nuclear, membranes.
4. Filter the tissue suspension through several nylon filters into an ice-cold beaker. The first filtration is through a 250-micron membrane; the second is through an 85-micron membrane; the third is through a 50-micron membrane; and the fourth is through a 20-micron membrane. Use a large funnel to hold the filters. Filtration can be sped up by gently squeezing the liquid through the filters.
5. Centrifuge the filtrate at 1200×g for 20 min. at 4° C. to pellet the nuclei.
6. Discard the dark green supernatant. The pellet will have several layers to it. One is starch; it is white and gritty. The nuclei are gray and soft. In the early steps, there may be a dark green and somewhat viscous layer of chloroplasts. Wash the pellets in about 25 ml cold H buffer (with Triton X-100) and resuspend by swirling gently and pipetting. After the pellets are resuspended.
   Pellet the nuclei again at 1200-1300×g. Discard the supernatant.
   Repeat the wash 3-4 times until the supernatant has changed from a dark green to a pale green. This usually happens after 3 or 4 resuspensions. At this point, the pellet is typically grayish white and very slippery. The Triton X-100 in these repeated steps helps to destroy the chloroplasts and mitochondria that contaminate the prep.
   Resuspend the nuclei for a final time in a total of 15 ml of H buffer and transfer the suspension to a sterile 125 ml Erlenmeyer flask.
7. Add 15 ml, dropwise, cold 2% Sarkosyl, 0.1 M Tris, 0.04 M EDTA solution (pH 9.5) while swirling gently. This lyses the nuclei. The solution will become very viscous.
8. Add 30 grams of CsCl and gently swirl at room temperature until the CsCl is in solution. The mixture will be gray, white and viscous.
9. Centrifuge the solution at 11,400×g at 4° C. for at least 30 min. The longer this spin is, the firmer the protein pellicle.
10. The result is typically a clear green supernatant over a white pellet, and (perhaps) under a protein pellicle. Carefully remove the solution under the protein pellicle and above the pellet. Determine the density of the solution by weighing 1 ml of solution and add CsCl if necessary to bring to 1.57 g/ml. The solution contains dissolved solids (sucrose etc) and the refractive index alone will not be an accurate guide to CsCl concentration.
11. Add 20 μl of 10 mg/ml EtBr per ml of solution.
12. Centrifuge at 184,000×g for 16 to 20 hours in a fixed-angle rotor.
13. Remove the dark red supernatant that is at the top of the tube with a plastic transfer pipette and discard. Carefully remove the DNA band with another transfer pipette. The DNA band is usually visible in room light; otherwise, use a long wave UV light to locate the band.
14. Extract the ethidium bromide with isopropanol saturated with water and salt. Once the solution is clear, extract at least two more times to ensure that all of the EtBr is gone. Be very gentle, as it is very easy to shear the DNA at this step. This extraction may take a while because the DNA solution tends to be very viscous. If the solution is too viscous, dilute it with TE.
15. Dialyze the DNA for at least two days against several changes (at least three times) of TE (10 mM Tris, 1 mM EDTA, pH 8) to remove the cesium chloride.
16. Remove the dialyzed DNA from the tubing. If the dialyzed DNA solution contains a lot of debris, centrifuge the DNA solution at least at 2500×g for 10 min. and carefully transfer the clear supernatant to a new tube. Read the A260 concentration of the DNA.
17. Assess the quality of the DNA by agarose gel electrophoresis (1% agarose gel) of the DNA. Load 50 ng and 100 ng (based on the OD reading) and compare it with known and good quality DNA. Undigested lambda DNA and a lambda-HindIII-digested DNA are good molecular weight makers.

Protocol for Digestion of Genomic DNA
Protocol:
1. The relative amounts of DNA for different crop plants that provide approximately a balanced number of genome equivalent is given in Table 3. Note that due to the size of the wheat genome, wheat DNA will be underrepresented. Lambda DNA provides a useful control for complete digestion.
2. Precipitate the DNA by adding 3 volumes of 100% ethanol. Incubate at −20° C. for at least two hours. Yeast DNA can be purchased and made up at the necessary concentration, therefore no precipitation is necessary for yeast DNA.

3. Centrifuge the solution at 11,400×g for 20 min. Decant the ethanol carefully (be careful not to disturb the pellet). Be sure that the residual ethanol is completely removed either by vacuum desiccation or by carefully wiping the sides of the tubes with a clean tissue.
4. Resuspend the pellet in an appropriate volume of water. Be sure the pellet is fully resuspended before proceeding to the next step. This may take about 30 min.
5. Add the appropriate volume of 10× reaction buffer provided by the manufacturer of the restriction enzyme to the resuspended DNA followed by the appropriate volume of enzymes. Be sure to mix it properly by slowly swirling the tubes.
6. Set-up the lambda digestion-control for each DNA that you are digesting.
7. Incubate both the experimental and lambda digests overnight at 37° C. Spin down condensation in a microfuge before proceeding.
8. After digestion, add 2 µl of loading dye (typically 0.25% bromophenol blue, 0.25% xylene cyanol in 15% Ficoll or 30% glycerol) to the lambda-control digests and load in 1% TPE-agarose gel (TPE is 90 mM Tris-phosphate, 2 mM EDTA, pH 8). If the lambda DNA in the lambda control digests are completely digested, proceed with the precipitation of the genomic DNA in the digests.
9. Precipitate the digested DNA by adding 3 volumes of 100% ethanol and incubating in −20° C. for at least 2 hours (preferably overnight).
   EXCEPTION: *Arabidopsis* and yeast DNA are digested in an appropriate volume; they don't have to be precipitated.
10. Resuspend the DNA in an appropriate volume of TE (e.g., 22 µl×50 blots=1100 µl) and an appropriate volume of 10× loading dye (e.g., 2.4 µl×50 blots=120 µl). Be careful in pipetting the loading dye—it is viscous. Be sure you are pipetting the correct volume.

TABLE 3

Some guide points in digesting genomic DNA.

| Species | Genome Size | Size Relative to *Arabidopsis* | Genome Equivalent to 2 µg *Arabidopsis* DNA | Amount of DNA per blot |
|---|---|---|---|---|
| *Arabidopsis* | 120 Mb | 1X | 1X | 2 µg |
| *Brassica* | 1,100 Mb | 9.2X | 0.54X | 10 µg |
| Corn | 2,800 Mb | 23.3X | 0.43X | 20 µg |
| Cotton | 2,300 Mb | 19.2X | 0.52X | 20 µg |
| Oat | 11,300 Mb | 94X | 0.11X | 20 µg |
| Rice | 400 Mb | 3.3X | 0.75X | 5 µg |
| Soybean | 1,100 Mb | 9.2X | 0.54X | 10 µg |
| Sugarbeet | 758 Mb | 6.3X | 0.8X | 10 µg |
| Sweetclover | 1,100 Mb | 9.2X | 0.54X | 10 µg |
| Wheat | 16,000 Mb | 133X | 0.08X | 20 µg |
| Yeast | 15 Mb | 0.12X | 1X | 0.25 µg |

Protocol for Southern Blot Analysis

The digested DNA samples are electrophoresed in 1% agarose gels in 1×TPE buffer. Low voltage; overnight separations are preferred. The gels are stained with EtBr and photographed.
1. For blotting the gels, first incubate the gel in 0.25 N HCl (with gentle shaking) for about 15 min.
2. Then briefly rinse with water. The DNA is denatured by 2 incubations. Incubate (with shaking) in 0.5 M NaOH in 1.5 M NaCl for 15 min.
3. The gel is then briefly rinsed in water and neutralized by incubating twice (with shaking) in 1.5 M Tris pH 7.5 in 1.5 M NaCl for 15 min.
4. A nylon membrane is prepared by soaking it in water for at least 5 min, then in 6×SSC for at least 15 min. before use. (20×SSC is 175.3 g NaCl, 88.2 g sodium citrate per liter, adjusted to pH 7.0.)
5. The nylon membrane is placed on top of the gel and all bubbles in between are removed. The DNA is blotted from the gel to the membrane using an absorbent medium, such as paper toweling and 6×SCC buffer. After the transfer, the membrane may be lightly brushed with a gloved hand to remove any agarose sticking to the surface.
6. The DNA is then fixed to the membrane by UV cross-linking and baking at 80° C. The membrane is stored at 4° C. until use.

B. Protocol for PCR Amplification of Genomic Fragments in *Arabidopsis*

Amplification Procedures:
1. Mix the following in a 0.20 ml PCR tube or 96-well PCR plate:

| Volume | Stock | Final Amount or Conc. |
|---|---|---|
| 0.5 µl | ~10 ng/µl genomic DNA[1] | 5 ng |
| 2.5 µl | 10X PCR buffer | 20 mM Tris, 50 mM KCl |
| 0.75 µl | 50 mM MgCl$_2$ | 1.5 mM |
| 1 µl | 10 pmol/µl Primer 1 (Forward) | 10 pmol |
| 1 µl | 10 pmol/µl Primer 2 (Reverse) | 10 pmol |
| 0.5 µl | 5 mM dNTPs | 0.1 mM |
| 0.1 µl | 5 units/µl Platinum Taq ™ (Life Technologies, Gaithersburg, MD) DNA Polymerase | 1 units |
| (to 25 µl) | Water | |

[1]*Arabidopsis* DNA is used in the present experiment, but the procedure is a general one.

2. The template DNA is amplified using a Perkin Elmer 9700 PCR machine:
1) 94° C. for 10 min. followed by

| 2) 5 cycles: | 3) 5 cycles: | 4) 25 cycles: |
|---|---|---|
| 94° C. - 30 sec | 94° C. - 30 sec | 94° C. - 30 sec |
| 62° C. - 30 sec | 58° C. - 30 sec | 53° C. - 30 sec |
| 72° C. - 3 min | 72° C. - 3 min | 72° C. - 3 min |

5) 72° C. for 7 min. Then the reactions are stopped by chilling to 4° C.

The procedure can be adapted to a multi-well format if necessary.

Quantification and Dilution of PCR Products:
1. The product of the PCR is analyzed by electrophoresis in a 1% agarose gel. A linearized plasmid DNA can be used as a quantification standard (usually at 50, 100, 200, and 400 ng). These will be used as references to approximate the amount of PCR products. HindIII-digested Lambda DNA is useful as a molecular weight marker. The gel can be run fairly quickly; e.g., at 100 volts. The standard gel is examined to determine that the size of the PCR products is consistent with the expected size and if there are significant extra bands or smeary products in the PCR reactions.
2. The amounts of PCR products can be estimated on the basis of the plasmid standard.

3. For the small number of reactions that produce extraneous bands, a small amount of DNA from bands with the correct size can be isolated by dipping a sterile 10-μl tip into the band while viewing though a UV Transilluminator. The small amount of agarose gel (with the DNA fragment) is used in the labeling reaction.

C. Protocol for PCR-DIG-Labeling of DNA

Solutions:

Reagents in PCR reactions (diluted PCR products, 10×PCR Buffer, 50 mM $MgCl_2$, 5 U/μl Platinum Taq Polymerase, and the primers)

10×dNTP+DIG-11-dUTP [1:5]: (2 mM dATP, 2 mM dCTP, 2 mM dGTP, 1.65 mM dTTP, 0.35 mM DIG-11-dUTP)

10×dNTP+DIG-11-dUTP [1:10]: (2 mM dATP, 2 mM dCTP, 2 mM dGTP, 1.81 mM dTTP, 0.19 mM DIG-11-dUTP)

10×dNTP+DIG-11-dUTP [1:15]: (2 mM dATP, 2 mM dCTP, 2 mM dGTP, 1.875 mM dTTP, 0.125 mM DIG-11-dUTP)

TE buffer (10 mM Tris, 1 mM EDTA, pH 8)

Maleate buffer: In 700 ml of deionized distilled water, dissolve 11.61 g maleic acid and 8.77 g NaCl. Add NaOH to adjust the pH to 7.5. Bring the volume to 1 L. Stir for 15 min. and sterilize.

10% blocking solution: In 80 ml deionized distilled water, dissolve 1.16 g maleic acid. Next, add NaOH to adjust the pH to 7.5. Add 10 g of the blocking reagent powder (Boehringer Mannheim, Indianapolis, Ind., Cat. no. 1096176). Heat to 60° C. while stirring to dissolve the powder. Adjust the volume to 100 ml with water. Stir and sterilize.

1% blocking solution: Dilute the 10% stock to 1% using the maleate buffer.

Buffer 3 (100 mM Tris, 100 mM NaCl, 50 mM $MgCl_2$, pH9.5). Prepared from autoclaved solutions of 1M Tris pH 9.5, 5 M NaCl, and 1 M $MgCl_2$ in autoclaved distilled water.

Procedure:

1. PCR reactions are performed in 25 μl volumes containing:

| PCR buffer | 1X |
|---|---|
| $MgCl_2$ | 1.5 mM |
| 10X dNTP + DIG-11-dUTP | 1X (please see the note below) |
| Platinum Taq ™ Polymerase | 1 unit |
| 10 pg probe DNA | |
| 10 pmol primer 1 | |

Note:

| | Use for: |
|---|---|
| 10X dNTP + DIG-11-dUTP (1:5) | <1 |
| 10X dNTP + DIG-11-dUTP (1:10) | 1 to 1.8 |
| 10X dNTP + DIG-11-dUTP (1:15) | >1.8 |

2. The PCR reaction uses the following amplification cycles:
1) 94° C. for 10 min.

| 2) 5 cycles: | 3) 5 cycles: | 4) 25 cycles: |
|---|---|---|
| 95° C. - 30 sec | 95° C. - 30 sec | 95° C. - 30 sec |
| 61° C. - 1 min | 59° C. - 1 min | 51° C. - 1 min |
| 73° C. - 5 min | 75° C. - 5 min | 73° C. - 5 min |

5) 72° C. for 8 min. The reactions are terminated by chilling to 4° C. (hold).

3. The products are analyzed by electrophoresis—in a 1% agarose gel, comparing to an aliquot of the unlabelled probe starting material.

4. The amount of DIG-labeled probe is determined as follows:

Make serial dilutions of the diluted control DNA in dilution buffer (TE: 10 mM Tris and 1 mM EDTA, pH 8) as shown in the following table:

| DIG-labeled control DNA starting conc. | Stepwise Dilution | Final Conc. (Dilution Name) |
|---|---|---|
| 5 ng/μl | 1 μl in 49 μl TE | 100 pg/μl (A) |
| 100 pg/μl (A) | 25 μl in 25 μl TE | 50 pg/μl (B) |
| 50 pg/μl (B) | 25 μl in 25 μl TE | 25 pg/μl (C) |
| 25 pg/μl (C) | 20 μl in 30 μl TE | 10 pg/μl (D) | a. Serial deletions of a DIG-labeled standard DNA ranging from 100 pg to 10 pg are spotted onto a positively charged nylon membrane, marking the membrane lightly with a pencil to identify each dilution.

b. Serial dilutions (e.g., 1:50, 1:2500, 1:10,000) of the newly labeled DNA probe are spotted.

c. The membrane is fixed by UV crosslinking.

d. The membrane is wetted with a small amount of maleate buffer and then incubated in 1% blocking solution for 15 min at room temp.

e. The labeled DNA is then detected using alkaline phosphatase conjugated anti-DIG antibody (Boehringer Mannheim, Indianapolis, Ind., cat. no. 1093274) and an NBT substrate according to the manufacture's instruction.

f. Spot intensities of the control and experimental dilutions are then compared to estimate the concentration of the PCR-DIG-labeled probe.

D. Prehybridization and Hybridization of Southern Blots

Solutions:

| 100% Formamide | purchased from Gibco |
|---|---|
| 20X SSC | (1X = 0.15M NaCl, 0.015M $Na_3$citrate) |
| per L: | 175 g NaCl |
| | 87.5 g $Na_3$citrate•$2H_2O$ |

20% Sarkosyl (N-lauroyl-sarcosine)

20% SDS (sodium dodecyl sulphate)

10% Blocking Reagent: In 80 ml deionized distilled water, dissolve 1.16 g maleic acid. Next, add NaOH to adjust the pH to 7.5. Add 10 g of the blocking reagent powder. Heat to 60° C. while stirring to dissolve the powder. Adjust the volume to 100 ml with water. Stir and sterilize.

Prehybridization Mix:

| Final Concentration | Components | Volume (per 100 ml) | Stock |
|---|---|---|---|
| 50% | Formamide | 50 ml | 100% |
| 5X | SSC | 25 ml | 20X |
| 0.1% | Sarkosyl | 0.5 ml | 20% |
| 0.02% | SDS | 0.1 ml | 20% |
| 2% | Blocking Reagent | 20 ml | 10% |
| | Water | 4.4 ml | |

General Procedures:

1. Place the blot in a heat-sealable plastic bag and add an appropriate volume of prehybridization solution (30 ml/100 $cm^2$) at room temperature. Seal the bag with a heat sealer, avoiding bubbles as much as possible. Lay down the bags in a large plastic tray (one tray can accommodate at least 4-5 bags). Ensure that the bags are lying flat in the tray so that the prehybridization solution is evenly distributed throughout the bag. Incubate the blot for at least 2 hours with gentle agitation using a waver shaker.
2. Denature DIG-labeled DNA probe by incubating for 10 min. at 98° C. using the PCR machine and immediately cool it to 4° C.
3. Add probe to prehybridization solution (25 ng/ml; 30 ml=750 ng total probe) and mix well but avoid foaming. Bubbles may lead to background.
4. Pour off the prehybridization solution from the hybridization bags and add new prehybridization and probe solution mixture to the bags containing the membrane.
5. Incubate with gentle agitation for at least 16 hours.
6. Proceed to medium stringency post-hybridization wash:
   Three times for 20 min. each with gentle agitation using 1×SSC, 1% SDS at 60° C.
   All wash solutions must be prewarmed to 60° C. Use about 100 ml of wash solution per membrane.
   To avoid background keep the membranes fully submerged to avoid drying in spots; agitate sufficiently to avoid having membranes stick to one another.
7. After the wash, proceed to immunological detection and CSPD development.

E. Procedure for Immunological Detection with CSPD Solutions:

| | |
|---|---|
| Buffer 1: | Maleic acid buffer (0.1M maleic acid, 0.15M NaCl; adjusted to pH 7.5 with NaoH) |
| Washing buffer: | Maleic acid buffer with 0.3% (v/v) Tween 20. |
| Blocking stock solution | Dissolve 10% blocking reagent in buffer 1. Dissolve (10X concentration): blocking reagent powder (Boehringer Mannheim, Indianapolis, IN, cat. no. 1096176) by constantly stirring on a 65° C. heating block or heat in a microwave, autoclave and store at 4° C. |
| Buffer 2 (1X blocking solution): | Dilute the stock solution 1:10 in Buffer 1. |
| Detection buffer: | 0.1M Tris, 0.1M NaCl, pH 9.5 |

Procedure:
1. After the post-hybridization wash the blots are briefly rinsed (1-5 min.) in the maleate washing buffer with gentle shaking.
2. Then the membranes are incubated for 30 min. in Buffer 2 with gentle shaking.
3. Anti-DIG-AP conjugate (Boehringer Mannheim, Indianapolis, Ind., cat. no. 1093274) at 75 mU/ml (1:10,000) in Buffer 2 is used for detection. 75 ml of solution can be used for 3 blots.
4. The membrane is incubated for 30 min. in the antibody solution with gentle shaking.
5. The membrane is washed twice in washing buffer with gentle shaking. About 250 mls is used per wash for 3 blots.
6. The blots are equilibrated for 2-5 min in 60 ml detection buffer.
7. Dilute CSPD (1:200) in detection buffer. (This can be prepared ahead of time and stored in the dark at 4° C.). The following steps must be done individually. Bags (one for detection and one for exposure) are generally cut and ready before doing the following steps.
8. The blot is carefully removed from the detection buffer and excess liquid removed without drying the membrane. The blot is immediately placed in a bag and 1.5 ml of CSPD solution is added. The CSPD solution can be spread over the membrane. Bubbles present at the edge and on the surface of the blot are typically removed by gentle rubbing. The membrane is incubated for 5 min. in CSPD solution.
9. Excess liquid is removed and the membrane is blotted briefly (DNA side up) on Whatman 3MM paper. Do not let the membrane dry completely.
10. Seal the damp membrane in a hybridization bag and incubate for 10 min at 37° C. to enhance the luminescent reaction.
11. Expose for 2 hours at room temperature to X-ray film. Multiple exposures can be taken. Luminescence continues for at least 24 hours and signal intensity increases during the first hours.

Example 3: Transformation of Carrot Cells

Transformation of plant cells can be accomplished by a number of methods, as described above. Similarly, a number of plant genera can be regenerated from tissue culture following transformation. Transformation and regeneration of carrot cells as described herein is illustrative.

Single cell suspension cultures of carrot (*Daucus carota*) cells are established from hypocotyls of cultivar Early Nantes in $B_5$ growth medium (O. L. Gamborg et al., *Plant Physiol.* 45:372 (1970)) plus 2,4-D and 15 mM $CaCl_2$ ($B_5$-44 medium) by methods known in the art. The suspension cultures are subcultured by adding 10 ml of the suspension culture to 40 ml of $B_5$-44 medium in 250 ml flasks every 7 days and are maintained in a shaker at 150 rpm at 27° C. in the dark.

The suspension culture cells are transformed with exogenous DNA as described by Z. Chen et al. *Plant Mol. Bio.* 36:163 (1998). Briefly, 4-days post-subculture cells are incubated with cell wall digestion solution containing 0.4 M sorbitol, 2% driselase, 5 mM MES (2[N-Morpholino] ethanesulfonic acid) pH 5.0 for 5 hours. The digested cells are pelleted gently at 60×g for 5 min. and washed twice in W5 solution containing 154 mM NaCl, 5 mM KCl, 125 mM $CaCl_2$ and 5 mM glucose, pH 6.0. The protoplasts are suspended in MC solution containing 5 mM MES, 20 mM $CaCl_2$, 0.5 M mannitol, pH 5.7 and the protoplast density is adjusted to about $4 \times 10^6$ protoplasts per ml.

15-60 µg of plasmid DNA is mixed with 0.9 ml of protoplasts. The resulting suspension is mixed with 40% polyethylene glycol (MW 8000, PEG 8000), by gentle inversion a few times at room temperature for 5 to 25 min. Protoplast culture medium known in the art is added into the PEG-DNA-protoplast mixture. Protoplasts are incubated in the culture medium for 24 hour to 5 days and cell extracts can be used for assay of transient expression of the introduced gene. Alternatively, transformed cells can be used to produce transgenic callus, which in turn can be used to produce transgenic plants, by methods known in the art. See, for example, Nomura and Komamine, *Plt. Phys.* 79:988-991 (1985), *Identification and Isolation of Single Cells that Produce Somatic Embryos in Carrot Suspension Cultures.*

A deposit of an *E. coli* Library, *E. coli* LibA021800, was made at the American Type Culture Collection in Manassas, Va., USA on Feb. 23, 2000 to meet the requirements of Budapest Treaty for the international recognition of the deposit of microorganisms. This deposit was assigned accession number PTA-1411.

A deposit of an *E. coli* Library, *E. coli* Lib060700, was made at the American Type Culture Collection in Manassas, Va., USA on Jun. 8, 2000 to meet the requirements of Budapest Treaty for the international recognition of the deposit of microorganisms. This deposit was assigned accession number PTA-2007.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

SEQUENCE LISTING

The patent contains a lengthy "Sequence Listing" section. A copy of the "Sequence Listing" is available in electronic form from the USPTO web site https://bulkdata.uspto.gov/data2/lengthysequencelisting/2018/. An electronic copy of the "Sequence Listing" will also be available from the USPTO upon request and payment of the fee set forth in 37 CFR 1.19(b)(3).

What is claimed is:

1. A recombinant nucleic acid comprising:
   a nucleic acid molecule having a nucleotide sequence which encodes a polypeptide comprising the amino acid sequence of SEQ ID NO:261, 733 or having at least 95% amino acid sequence identity to the amino acid sequence of SEQ ID NO:261, 733;
   wherein the polypeptide encodes a Dof zinc finger protein;
   wherein the nucleic acid molecule is operably linked to a heterologous regulatory sequence.

2. The recombinant nucleic acid according to claim 1, wherein the nucleic acid molecule comprises the nucleotide sequence of SEQ ID NO:261, 732.

3. The recombinant nucleic acid according to claim 1, wherein the nucleic acid molecule encodes a polypeptide comprising the amino acid sequence of SEQ ID NO:261, 733.

4. A vector construct comprising the recombinant nucleic acid of claim 1.

5. A host cell comprising the recombinant nucleic acid molecule according to claim 1.

6. A host cell comprising a vector construct according to claim 4.

7. A method of introducing recombinant nucleic acid into a host cell comprising:

a) providing the recombinant nucleic acid according to claim 1; and
   b) contacting said recombinant nucleic acid with said host cell under conditions that permit insertion of said recombinant nucleic acid into said host cell.

8. A method of transforming a host cell which comprises contacting the host cell with the vector construct according to claim 4.

9. A plant, plant cell, plant material or seed of a plant which comprises the recombinant nucleic acid according to claim 1.

10. A plant, plant cell, plant material or seed of a plant which comprises a vector construct according to claim 4, wherein the plant, plant cell, plant material or seed comprises the recombinant nucleic acid.

11. A plant that has been regenerated from a plant cell or seed according to claim 9 or 10, wherein the plant comprises the recombinant nucleic acid.

12. Transgenic progeny of the plant of claim 9 or 10, wherein the progeny comprises the recombinant nucleic acid.

13. Seed from the plant according to claim 9, wherein the seed comprises the recombinant nucleic acid.

* * * * *